US011553876B2

(12) United States Patent
Brown et al.

(10) Patent No.: US 11,553,876 B2
(45) Date of Patent: *Jan. 17, 2023

(54) REVERSAL OF GENERAL ANESTHESIA BY ADMINISTRATION OF METHYLPHENIDATE, AMPHETAMINE, MODAFINIL, AMANTADINE, AND/OR CAFFEINE

(71) Applicant: The General Hospital Corporation, Boston, MA (US)

(72) Inventors: Emery N. Brown, Brookline, MA (US); Patrick L. Purdon, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 781 days.

This patent is subject to a terminal disclaimer.

(21) Appl. No.: 16/373,498

(22) Filed: Apr. 2, 2019

(65) Prior Publication Data

US 2019/0290196 A1    Sep. 26, 2019

Related U.S. Application Data

(63) Continuation of application No. 14/618,978, filed on Feb. 10, 2015, now Pat. No. 10,299,720, which is a
(Continued)

(51) Int. Cl.
  *G01N 33/48*  (2006.01)
  *A61B 5/00*   (2006.01)
(Continued)

(52) U.S. Cl.
  CPC ............ *A61B 5/4821* (2013.01); *A61B 5/316* (2021.01); *A61B 5/369* (2021.01); *A61K 31/13* (2013.01);
(Continued)

(58) Field of Classification Search
  CPC combination set(s) only.
  See application file for complete search history.

(56) References Cited

U.S. PATENT DOCUMENTS 2,507,631 A   5/1950   Harlann et al.
2,957,880 A   10/1960  Rometsch
(Continued)

FOREIGN PATENT DOCUMENTS

EP   0765630 A1    4/1997
JP   2008178546 A  8/2008
(Continued)

OTHER PUBLICATIONS

Sartori, et al., On-Line Estimation of Propofol Pharmacodynamic Parameters, Proceedings of the 2005 IEEE Engineering in Medicine and Biology 27th Annual Conference, 2005, pp. 74-77.
(Continued)

*Primary Examiner* — Layla Soroush
(74) *Attorney, Agent, or Firm* — Quarles & Brady LLP

(57) ABSTRACT

The present invention generally relates to compositions comprising anesthesia-reversing agents which facilitate or increase the time of awakening or reverse the effects of general anesthesia-induced unconsciousness. In some embodiments, the anesthesia reversing agent can be selected from any or a combination of methylphenidate (MPH), amphetamine, modafinil, amantadine, caffeine, or analogues or derivatives thereof. In some embodiments, compositions comprising at least one or more anesthesia-reversing agents can be used to facilitate awakening from anesthesia without or decreasing occurrence of delirium, and can be used in methods to treat or prevent the symptoms associated with emergence delirium, as well as treat a subject oversedated with general an esthesia. The invention also relates to
(Continued)

methods for administering these compositions comprising anesthesia-reversing agents to subjects and for use.

11 Claims, 8 Drawing Sheets

Related U.S. Application Data continuation of application No. 13/819,924, filed as application No. PCT/US2011/050213 on Sep. 1, 2011, now abandoned.

(60) Provisional application No. 61/483,476, filed on May 6, 2011, provisional application No. 61/378,977, filed on Sep. 1, 2010.

(51) Int. Cl.

| | |
|---|---|
| A61K 31/13 | (2006.01) |
| A61K 31/137 | (2006.01) |
| A61K 31/165 | (2006.01) |
| A61K 31/522 | (2006.01) |
| A61K 45/06 | (2006.01) |
| A61B 5/316 | (2021.01) |
| A61B 5/369 | (2021.01) |
| A61K 31/4458 | (2006.01) |
| A61K 9/00 | (2006.01) |

(52) U.S. Cl.
CPC .......... *A61K 31/137* (2013.01); *A61K 31/165* (2013.01); *A61K 31/4458* (2013.01); *A61K 31/522* (2013.01); *A61K 45/06* (2013.01); *A61K 9/0019* (2013.01)

(56) References Cited

U.S. PATENT DOCUMENTS

| | | | |
|---|---|---|---|
| 4,195,643 | A | 4/1980 | Pratt, Jr. |
| 4,392,849 | A | 7/1983 | Petre et al. |
| 4,448,199 | A | 5/1984 | Schmid |
| 4,911,167 | A | 3/1990 | Corenman et al. |
| 5,195,530 | A | 3/1993 | Shindel |
| 5,851,438 | A | 12/1998 | Chan |
| 5,908,850 | A | 6/1999 | Zeitlin et al. |
| 6,025,362 | A | 2/2000 | Fukunaga et al. |
| 6,032,063 | A | 2/2000 | Hoar et al. |
| 6,032,065 | A | 2/2000 | Brown |
| 6,067,467 | A | 5/2000 | John |
| 6,281,242 | B1 | 8/2001 | Regan et al. |
| 6,338,713 | B1 | 1/2002 | Chamoun et al. |
| 6,708,051 | B1 | 3/2004 | Durousseau |
| 6,740,214 | B1 | 5/2004 | Dobson et al. |
| 6,944,565 | B2 | 9/2005 | Meneilage et al. |
| 7,006,872 | B2 | 2/2006 | Gielen et al. |
| 7,286,871 | B2 | 10/2007 | Cohen |
| 7,783,343 | B2 | 8/2010 | Sarkela et al. |
| 3,025,404 | A1 | 9/2011 | Bolger et al. |
| 8,073,534 | B2 | 12/2011 | Low |
| 8,244,526 | B2 | 8/2012 | Vos et al. |
| 8,298,154 | B2 | 10/2012 | Hete et al. |
| 8,315,970 | B2 | 11/2012 | Zalay et al. |
| 8,521,294 | B2 | 8/2013 | Sarma et al. |
| 8,630,722 | B2 | 1/2014 | Condurso et al. |
| 2002/0128798 | A1 | 9/2002 | Lange et al. |
| 2002/0156357 | A1 | 10/2002 | Axelgaard |
| 2003/0088167 | A1 | 5/2003 | Fendrock et al. |
| 2003/0130585 | A1 | 7/2003 | Wenger |
| 2004/0143021 | A1 | 7/2004 | Larijani |
| 2004/0193068 | A1 | 9/2004 | Burton et al. |
| 2005/0054941 | A1 | 3/2005 | Ting et al. |
| 2006/0135880 | A1 | 6/2006 | Sarkela |
| 2006/0178585 | A1 | 8/2006 | Sharrock |
| 2006/0229519 | A1 | 10/2006 | Fujiwara et al. |
| 2007/0067003 | A1 | 3/2007 | Sanchez et al. |
| 2007/0073355 | A1 | 3/2007 | DiLorenzo |
| 2007/0100389 | A1 | 5/2007 | Jaax et al. |
| 2007/0123468 | A1 | 5/2007 | Jenkins |
| 2007/0150025 | A1 | 6/2007 | DiLorenzo et al. |
| 2007/0167694 | A1 | 7/2007 | Causevic et al. |
| 2007/0191704 | A1 | 8/2007 | DeCharms |
| 2007/0203540 | A1 | 8/2007 | Goetz et al. |
| 2008/0021345 | A1 | 1/2008 | Kern et al. |
| 2008/0249431 | A1 | 10/2008 | Bier et al. |
| 2008/0306397 | A1 | 12/2008 | Bonmassar et al. |
| 2010/0023089 | A1 | 1/2010 | DiLorenzo |
| 2010/0280333 | A1 | 11/2010 | Parshuram et al. |
| 2011/0044524 | A1 | 2/2011 | Wang et al. |
| 2011/0082381 | A1 | 4/2011 | Uthman et al. |
| 2011/0125046 | A1 | 5/2011 | Burton et al. |
| 2011/0137134 | A1 | 6/2011 | Hemmerling et al. |
| 2011/0137297 | A1 | 6/2011 | Kiani et al. |
| 2011/0218454 | A1 | 9/2011 | Low |
| 2011/0224570 | A1 | 9/2011 | Causevic |
| 2012/0022391 | A1 | 1/2012 | Leuthardt |
| 2012/0029378 | A1 | 2/2012 | Low |
| 2012/0101401 | A1 | 4/2012 | Faul et al. |
| 2012/0250963 | A1 | 10/2012 | Carroll et al. |
| 2013/0131464 | A1 | 5/2013 | Westbrook et al. |
| 2013/0197339 | A1 | 8/2013 | Bardakjian et al. |
| 2013/0211224 | A1 | 8/2013 | Isenhart et al. |
| 2013/0310422 | A1 | 11/2013 | Brown et al. |
| 2013/0331660 | A1 | 12/2013 | Al-Ali et al. |
| 2014/0012100 | A1 | 1/2014 | Al-Ali et al. |
| 2014/0180160 | A1 | 6/2014 | Brown et al. |
| 2014/0187973 | A1 | 7/2014 | Brown et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2014/0371548 | A1 | 12/2014 | Al-Ali et al. |
| 2015/0011907 | A1 | 1/2015 | Purdon et al. |
| 2015/0080754 | A1 | 3/2015 | Purdon et al. |

FOREIGN PATENT DOCUMENTS

| | | |
|---|---|---|
| RU | 95243 U1 | 6/2010 |
| WO | 2004036379 A2 | 4/2004 |
| WO | 2004037114 A2 | 5/2004 |
| WO | 2004047632 A1 | 6/2004 |
| WO | 2012145285 A1 | 10/2012 |
| WO | 2012154701 A1 | 11/2012 |

OTHER PUBLICATIONS

Sawaguchi, et al., A Model-Predictive Hypnosis Control System Under Total Intravenous Anesthesia, IEEE Transactions on Biomedical Engineering, 2008, 55(3):874-887.

Schaffer, et al., The Effect of the Atmosphere and the Role of Pore Filling on the Sintering of Aluminum, Acta Materialia, 2006, 54(1):131-138.

Schwilden, et al., Closed-Loop Feedback Control of Methohexital Anesthesia by Quantitative EEG Analysis in Humans, Anesthesiology, 1987, 67:341-347.

Schwilden, et al., Closed-Loop Feedback Control of Propofol Anaesthesia by Quantitative EEG Analysis in Humans, Br. J. Anaesth, 1989, 62:290-296.

Struys, et al., Comparison of Closed-Loop Controlled Administration of Propofol Using Bispectral Index as the Controlled Variable Versus "Standard Practice" Controlled Administration, Anesthesiology, 2001, 95(1):6-17.

Struys, et al., Closed Loops in Anaesthesia, Best Practice & Research Clinical Anaesthesiology, 2006, 20(1):211-220.

Tan, et al., Sparse Learning Via Iterative Minimization With Application to MIMO Radar Imaging, IEEE Transactions on Signal Processing, 2011, 59(3):1088-1101.

Truccolo, et al., A Point Process Framework for Relating Neural Spiking Activity to Spiking History, Neural Ensemble, and Extrinsic Covariate Effects, J Neurophysiol., 2005, 93:1074-1089.

(56) References Cited

OTHER PUBLICATIONS

Van Vugt, Comparison of Spectral Analysis Methods for Characterizing Brain Oscillations, J. Neurosci. Methods, 2007, 162(1-2):49-63.
Vijn, et al., I.v. Anaesthesia and EEG Burst Suppression in Rats: Bolus Injections and Closed-Loop Infusions, British Journal of Anaesthesia, 1998, 81:415-421.
Vusanovic, et al., Microsegregation Phenomena in Al—Cu—Mg Alloy with Considering of Diffusion Phenomena in Primary Phase, Facta Universitatis, Series: Mechanical Engineering, 2001, 1(8):965-980.
Wang, et al., Precipitates and Intermetallic Phases in Precipitation and Hardening Al—Cu—Mg—(Li) Based Alloys, International Materials Reviews, 2005, 50(4):193-215.
Zdunek, et al., Improved M-FOCUSS Algorithm With Overlapping Blocks for Locally Smooth Sparse Signals, IEEE Transactions on Signal Processing, 2008, 56(10):4752-4761.
Article: "Polyesters", http://web.archive.org/web/20020812093256/http://pslc.ws/macrog/pet.htm, Copyright 1995, 1996 Department of Polymer Science, University of Southern Mississippi, 4 pages.
European Patent Office, Extended European Search Report, Application No. 12781958.9, dated Sep. 15, 2014, 12 pages.
PCT International Search Report and Written Opinion, PCT/US2005/042401, dated Jun. 14, 2006,17 pages.
PCT International Search Report and Written Opinion, PCT/US2009/062072, dated May 12, 2010, 13 pages.
PCT International Search Report and Written Opinion, PCT/US2011/050213, dated May 1, 2012, 12 pages.
PCT International Search Report and Written Opinion, PCT/US2012/036854, dated Aug. 16, 2012, 6 pages.
PCT International Search Report and Written Opinion, PCT/US2013/064852, dated Jan. 23, 2014, 6 pages.
PCT International Search Report and Written Opinion, PCT/US2014/033619, dated Sep. 23, 2014, 12 pages.
PCT International Search Report and Written Opinion, PCT/US2014/035166, dated Aug. 29, 2014, 17 pages.
PCT International Search Report and Written Opinion, PCT/US2014/035178, dated Sep. 15, 2014, 15 pages.
PCT International Search Report and Written Opinion, PCT/US2014/035319, dated Sep. 26, 2014, 15 pages.
PCT International Search Report and Written Opinion, PCT/US2014/035329, dated Sep. 26, 2014, 11 pages.
PCT International Search Report and Written Opinion, PCT/US2014/035333, dated Sep. 26, 2014, 14 pages.
PCT International Search Report and Written Opinion, PCT/US2014/044692, dated Nov. 4, 2014, 12 pages.
PCT International Search Report and Written Opinion, PCT/US2014/044720, dated Nov. 28, 2014, 13 pages.
PCT International Search Report and Written Opinion, PCT/US2014/055509, dated Dec. 2, 2014, 15 pages.
PCT International Search Report and Written Opinion, PCT/US2014/064144, dated Jan. 27, 2015, 7 pages.
Babadi et al., A Review of Multitaper Spectral Analysis, IEEE Transactions on Biomedical Engineering, 2014, 61(5):1555-1564.
Absalom, et al., Closed-Loop Control of Anesthesia Using Bispectral Index, Anesthesiology, 2002, 96(1):67-73.
Absalom, et al., Closed Loop Anesthesia: Are We Getting Close to Finding the Holy Grail?, Anesthesia & Analgesia, 2011, 112(3):516-518.
Andrews, et al., The Chronux Manual, Aug. 16, 2008, 178 pages.
Araki, et al., Computer Control of Physiological States of Patients Under and After Surgical Operation, Annual Reviews in Control, 2005, 29:229-236.
Barras, et al., Total Intravenous Anesthesia on the Battlefield, The Army Medical Department Journal, 2009, pp. 68-72.
Bellville, et al., Servo Control of General Anesthesia, Science, 1957,126:827-830.
Besch, et al., Occurrence of and Risk Factors for Electroencephalogram Burst Suppression During Propofol-Remifentanil Anaesthesia, British Journal of Anaesthesia, Advance Access Published Aug. 8, 2011, 8 pages.
Besthorn, et al., EEG Coherence in Alzheimer Disease, Electroencephalography and Clinical Neurophysiology, 1994, 90:242-245.
Bickford, Automatic Electroencephalographic Control of General Anesthesia, EEG Clin. Neurophysiol., 1950, 2:93-96.
Bickford, Use of Frequency Discrimination in the Automatic Electroencephalographic Control of Anesthesia (ServoAnesthesia), EEG Clin. Neurophysiol., 1951, 3:83-86.
Blanco, et al., Time-Frequency Analysis of Electroencephalogram Series. III. Wavelet Packets and Information Cost Function, Physical Review E, 1998, 57(1):932-940.
Bonmassar, Resistive Tapered Stripline (RTS) in Electroencephalogram Recordings During MRI, IEEE Transactions on Microwave Theory and Techniques, 2004, 52(8):1992-1998.
Bourguignon, et al., A Sparsity-Based Method for the Estimation of Spectral Lines From Irregularly Sampled Data, IEEE Journal of Selected Topics in Signal Processing, 2007, 1(4):575-585.
Breshears, et al., Stable and Dynamic Cortical Electrophysiology of Induction and Emergence with Propofol Anesthesia, PNAS, 2010, 107(49):21170-21175.
Candes, et al., Enhancing Sparsity by Reweighted l1 Minimization, J. Fourier Anal. Appl., 2008, 14:877-905.
Chemali, et al., Burst Suppression Probability Algorithms: State-Space Methods for Tracking EEG Burst Suppression, J. Neural Eng., 2013, 10(5):056017.
Ching, et al., A Neurophysiological-Metabolic Model for Burst Suppression, PNAS, 2012,109(8):3095-3100.
Cimenser, et al., Tracking Brain States Under General Anesthesia by Using Global Coherence Analysis, PNAS, 2011, 108(21):8832-8837.
Ciuciu, et al., A Half-Quadratic Block-Coordinate Descent Method for Spectral Estimation, Signal Processing, 2002, 82:941-959.
Cotten, et al., Closed-Loop Continuous Infusions of Etomidate and Etomidate Analogs in Rats, Anesthesiology, 2011, 115(4):764-773.
Dodson, et al., Postoperative Effects of Methylphenidate, British Journal of Anaesthesia, 1980, 52:1265-1270.
Gentilini, et al., Modeling and Closed-Loop Control of Hypnosis by Means of Bispectral Index (BIS) with Isoflurane, IEEE Transactions on Biomedical Engineering, 2001, 48(8):874-889.
Glass, Automated Control of Anesthesia Ten Years Later: Futuristic Novelty or Present Day Reality, Can. J. Anesth./J. Can. Anesth., 2010, 57:715-719.
Goldman, et al., Acquiring Simultaneous EEG and Functional MRI, Clinical Neurophysiology, 2000, 111:1974-1980.
Hahn, et al., Closed-Loop Anesthetic Drug Concentration Estimation Using Clinical-Effect Feedback, IEEE Transactions on Biomedical Engineering, 2011, 58(1):3-6.
Hahn, et al., A Direct Dynamic Dose-Response Model of Propofol for Individualized Anesthesia Care, Journal of Latex Class Files, 2007, 6(1):1-8.
Hemmerling, et al., A Randomized Controlled Trial Demonstrates that a Novel Closed-Loop Propofol System Performs Better Hypnosis Control than Manual Administration, Can. J. Anesth./J. Can. Anesth., 2010, 57:725-735.
John, et al., Invariant Reversible QEEG Effects of Anesthetics, Consciousness and Cognition, 2001, 10:165-183.
Lemieux, et al., Recording of EEG During fMRI Experiments: Patient Safety, MRM, 1997, 38:943-952.
Leslie, et al., Closed Loop Control of Sedation for Colonoscopy Using the Bispectral Index, Anaesthesia, 2002, 57:690-709.
Liley, et al., Propofol and Remifentanil Differentially Modulate Frontal Electroencephalographic Activity, Anesthesiology, 2010, 113:292-304.
Lin, et al., EEG-Based Drowsiness Estimation for Safety Driving Using Independent Component Analysis, IEEE Transactions on Circuits and Systems-I: Regular Papers, 2005, 52(12):2726-2738.
Liu, et al., Titration of Propofol for Anesthetic Induction and Maintenance Guided by the Bispectral Index: Closed-Loop Versus Manual Control, Anesthesiology, 2006, 104:686-695.

(56) References Cited

OTHER PUBLICATIONS

Liu, et al., Feasibility of Closed-Loop Titration of Propofol Guided by the Bispectral Index for General Anaesthesia Induction: A Prospective Randomized Study, European Journal of Anaesthesiology, 2006, 23:465-469.

Liu, et al., Neural Origin of Spontaneous Hemodynamic Fluctuations in Rats Under Burst-Suppression Anesthesia Condition, Cerebral Cortex, 2011, 21:374-384.

Locher, et al., A New Closed-Loop Control System for Isoflurane Using Bispectral Index Outperforms Manual Control, Anesthesiology, 2004, 101:591-602.

Lotte, et al., A Review of Classification Algorithms for EEG-Based Brain-Computer Interfaces, Journal of Neural Engineering, 2007, 4:R1-R13.

Martin, et al., Investigating Neural-Hemodynamic Coupling and the Hemodynamic Response Function in the Awake Rat, NeuroImage, 2006, 32:33-48.

Misattari, et al., Treatment of Refractory Status Epilepticus With Inhalational Anesthetic Agents Isoflurane and Desflurane, Arch. Neurol., 2004, 61:1254-1259.

Molaee-Ardekani, et al., Delta Waves Differently Modulate High Frequency Components of EEG Oscillations in Various Unconsciousness Levels, Proceedings of the 29th Annual International Conference of the IEEE EMBS, 2007, pp. 1294-1297.

Morley, et al., Closed Loop Control of Anaesthesia: An Assessment of the Bispectral Index as the Target of Control, Anaesthesia, 2000, 55:953-959.

Mortier, et al., Closed-Loop Controlled Administration of Propofol Using Bispectral Analysis, Anesthesia, 1998, 53:749-754.

Orsini, et al., Propofol Infusion Syndrome: Case Report and Literature Review, Am. J. Health-Syst. Pharm., 2009, 66:908-915.

Pritchett, et al., Power Analysis of Gamma Frequencies (30-47Hz), Adjusting for Muscle Activity (80-97Hz), in Anesthesia: A Comparison Between Young Adults, Middle-Aged and the Elderly, 30th Annual International IEEE EMBS Conference, 2008, pp. 825-830.

Purdon, Multimodal Neuroimaging with Simultaneous Electroencephalogram and High-Field Functional Magnetic Resonance Imaging, Master Thesis Submitted to the Harvard-MIT Division of Health Sciences and Technology, Jun. 2005.

Purdon, et al., Electroencephalogram Signatures of Loss and Recovery of Consciousness from Propofol, PNAS, Published Online Mar. 4, 2013, pp. E1142-E1151.

Puri, et al., Closed-Loop Anaesthesia Delivery System (CLADS(TM)) Using Bispectral Index: A Performance Assessment Study, Anaesthesia and Intensive Care, 2007, 35(3):357-362.

Roche-Labarbe, et al., Coupled Oxygenation Oscillation Measured by NIRS and Intermittent Cerebral Activation on EEG in Premature Infants, NeuroImage, 2007, 36:718-727.

Rossetti, et al., Refractory Status Epilepticus, Effect of Treatment Aggressiveness on Prognosis, Arch. Neurol., 2005, 62:1698-1702.

Sacchi, et al., Interpolation and Extrapolation Using a High-Resolution Discrete Fourier Transform, IEEE Transactions on Signal Processing, 1998, 46(1):31-38.

FIG. 4A Awake (room air)
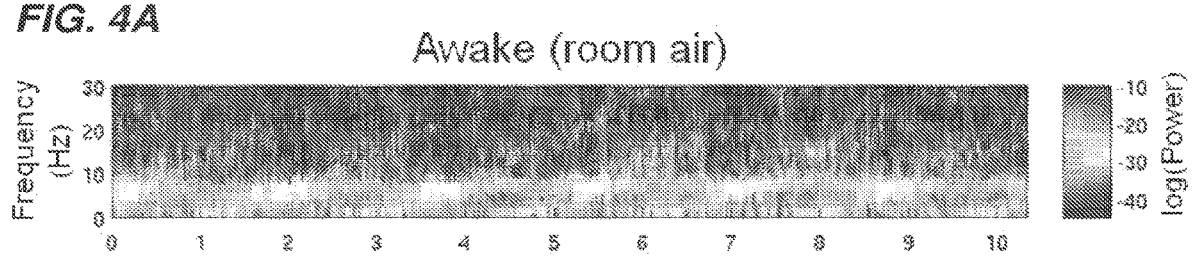
FIG. 4B Continuous inhalation of isoflurane (1.0%)
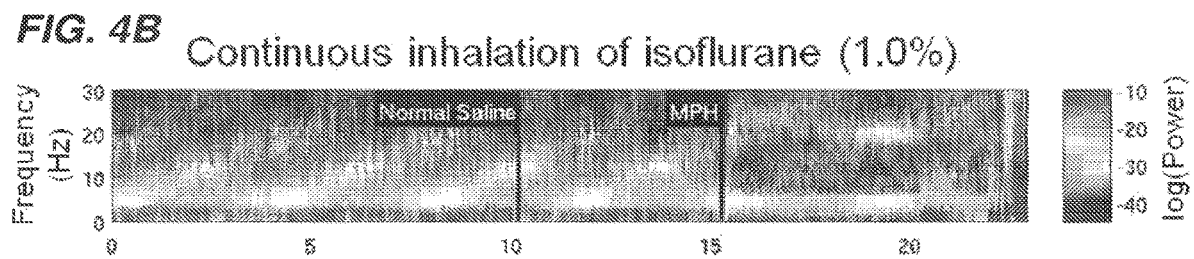
FIG. 4C Continuous inhalation of isoflurane (1.0%)
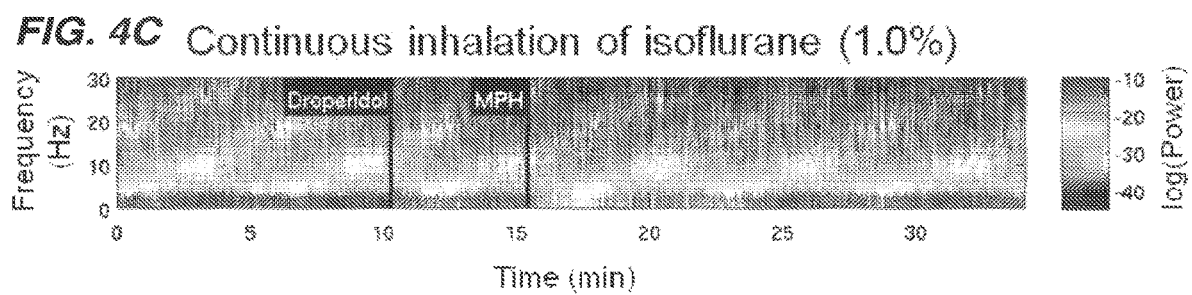
Time (min)

REVERSAL OF GENERAL ANESTHESIA BY ADMINISTRATION OF METHYLPHENIDATE, AMPHETAMINE, MODAFINIL, AMANTADINE, AND/OR CAFFEINE

CROSS REFERENCE TO RELATED APPLICATIONS

This application claims priority under 35 U.S.C. 119(e) of U.S. Provisional Patent Application Ser. No. 61/378,977 filed on Sep. 1, 2010, and U.S. Provisional Patent Application Ser. No. 61/483,475 filed on May 6, 2011, the contents of each are incorporated herein by reference in their entirety.

GOVERNMENT SUPPORT

The present application was made with Government Support under Grant No: DP1-OD003646, K08-GM094394 and K08-GM083216 awarded by the National Institutes of Health (NIH). The Government of the United States has certain rights thereto.

FIELD OF THE INVENTION

The present invention relates to a method and compositions for rapidly reversing general anesthesia, and facilitates awakening of a subject from general anesthesia. In particular, the present invention relates to a method and compositions for facilitating emergence or awakening from perioperative anesthesia, and a method for controlling and facilitating anesthesia according to the methods and compositions as disclosed herein.

BACKGROUND OF THE INVENTION

General anesthesia is a reversible coma, actively induced and maintained by administering intravenous and inhalational drugs.[1] In contrast, emergence from general anesthesia is a slow passive process achieved simply by allowing the effects of the drug to wear off. Emergence of anesthesia is therefore a passive process whereby anesthetic drugs are merely discontinued at the end of surgery, and no drugs are administered to actively reverse their effects on the brain and central nervous system. That is, the general anesthetic agents are merely discontinued at the end of surgery, leaving the anesthesiologist and surgeon to wait for the patient to recover consciousness. The timing of emergence can be unpredictable because many factors including the nature and duration of the surgery, and the age, physical condition and body habitus of the patient, can greatly affect the pharmacokinetics and pharmacodynamics of general anesthetics. Although the actions of many drugs used in anesthesiology are pharmacologically reversed when no longer desired (e.g. muscle relaxants, opioids, benzodiazepines, and anticoagulants), this is not the case for general anesthetic induced loss of consciousness.

This current clinical paradigm of passive emergence is dangerous because patients are highly susceptible to potentially severe complications such as laryngospasm, respiratory depression, hemodynamic instability, and delirium. In addition, operating room (OR) time, estimated to cost between $12.37 to $17.11 per minute at MGH, is an expensive resource that is squandered during the time spent waiting for patients to emerge from general anesthesia.

At present, there is no agent available to actively induce emergence from general anesthesia. This is largely due to our limited knowledge of the molecular mechanisms of general anesthetic actions, hampering the development of drugs that antagonize the actions of general anesthetics. However, accumulating evidence suggests that ascending arousal pathways in the brain can play important roles in emergence from general anesthesia.[2] While cholinergic,[3,4] Aorexinergic,[5] and histaminergic[6] arousal pathways have been implicated in emergence, the roles of other arousal pathways are yet unknown. Methylphenidate is widely prescribed for the treatment of Attention Deficit Hyperactivity Disorder (ADHD) in children and adults, and acts primarily by inhibiting the dopamine and norepinephrine reuptake transporters,[7] thereby increasing dopaminergic and adrenergic neurotransmission. Recently, methylphenidate has also been reported to increase prefrontal cortex histamine levels in rats.[8] Dopamine, norepinephrine, and histamine are monoamine neurotransmitters that promote arousal through pathways emanating from nuclei in the pons, midbrain and hypothalamus.[2,9]

SUMMARY OF THE INVENTION

The present invention relates to agents which function as general anesthesia emerging agents for a method to awaken a subject from general anesthesia. In some embodiments, the anesthesia-reversing agents as disclosed herein are useful as a "rescue" drug, or a method to rescue subjects who are accidentally oversedated and become unresponsive or apneic during conscious sedation.

One embodiment of the present invention relates to a method of reducing the effects of general anesthesia in a subject (e.g., a human patient) treated with a general anesthetic agent comprising administering to the subject an effective amount of a composition comprising an anesthesia-reversing agents as disclosed herein, thereby reducing the effects of general anesthesia in the subject. In some embodiments, an anesthesia-reversing agent can be selected from one or more or any combination of: methylphenidate (MPH), amphetamine, modafinil, amantadine, caffeine or a product containing any of these agents. In some embodiments, amphetamine is dextro-amphetamine (D-amphetamine). In some embodiments, amphetamine is levo-amphetamine (L-amphetamine). In some embodiments, a composition can comprise a plurality of anesthesia-reversing agents, e.g., at least 2 or at least 3, or at least 4, or at least 5, or at least 6, or at least 7, or more anesthesia-reversing agents.

Without wishing to be limited to theory, the effects of general anesthesia induces the subject to unconsciousness, and emerge from anesthesia occurs as a passive process after withdrawal or cessation of anesthesia administration. The present invention provides anesthesia-reversing agents and methods of use to greatly facilitate the speed of emergence from general anesthesia, and restoration of mobility or consciousness in the subject, without waiting for the passive process of the general anesthesia agents to wear off. The present invention of using the anesthesia-reversing agents as disclosed herein reduces the effects of general anesthesia thereby reduces or eliminates the effects of emergence delirium in the subject.

In some embodiments, the compositions comprising the anesthesia-reversing agents, and their method of use to awaken a subject from anesthesia can be used to reverse a subject from any form of anesthesia agent. In some embodiments, the anesthetic agent is isoflurane; which results in unconsciousness or diminished arousal in the subject, and in some embodiments, the compositions comprising the anesthesia-reversing agents, and their method of use can be used to reverse the unconsciousness or diminished arousal in the subject.

Herein, the inventors have demonstrated that methylphenidate (MPH) and analogues and derivatives thereof induces emergence of a subject from anesthesia-induced unconsciousness, e.g., from isoflurane or propofol induced anesthesia and other anesthesia agents in rats by increasing arousal and respiratory drive. Accordingly, one aspect of the present invention relates to use of methylphenidate as a clinically useful as an agent to reverse general anesthetic-induced unconsciousness and respiratory depression at the end of surgery.

Accordingly, in one embodiment, an anesthesia-reversing agent is MPH, and in some embodiments, MPH is dextro-methylphenidate (D-MPH). In some embodiments, a methods and compositions as disclosed herein can comprise D-MPH and L-MPH anesthesia-reversing agents. In some embodiments, the methods and compositions as disclosed herein can comprise D-MPH and L-MPH anesthesia-reversing agents in equal or different ratios, e.g., about 50%:50%, or about 60%:40%, or about 70%:30%, or 80%:20%, 90%:10%, 95%:5% etc. or any other ratio, of D-MPH:L-MPH or vice versa, e.g., of L-MPH:D-MPH.

In some embodiments, compositions comprising the anesthesia-reversing agents, and their method of use to reverse the anesthesia of a subject can be administered by intravenous dose. In some embodiments, compositions comprising the anesthesia-reversing agents, and their method of use to awaken a subject from anesthesia can be administered by any form, e.g., by inhalation and the like.

One aspect of the present invention relates to a method of facilitating emergence from general anesthesia in a subject treated with a general anesthetic agent comprising administering to the subject an effective amount of a composition comprising at least one anesthesia-reversing agent, wherein the anesthesia-reversing agent facilitates emergence of the subject from the general anesthesia. In some embodiments, the anesthesia-reversing agent is selected from any or a combination of methylphenidate (MPH), amphetamine, modafinil, amantadine, or caffeine. In some embodiments, the anesthesia-reversing agent is a methylphenidate, which is dextro-methylphenidate (D-MPH) or levo-methylphenidate (L-MPH) or a combination thereof, or an analogue or derivative thereof. In some embodiments, the methylphenidate is racemic methylphenidate. In some embodiments, the anesthesia-reversing agent is amphetamine, which can be L-amphetamine.

In some embodiments, the emergence of the subject from general anesthesia comprises restoration of mobility or consciousness in the subject, and/or reducing or eliminating the effects of delirium on emergence of the subject from the general anesthesia.

In some embodiments, the anesthesia-reversing agent is effective at facilitating awakening or emergence from anesthesia, e.g., from a general anesthetic agent which is administered to the subject by inhalation anesthesia. In some embodiments, a general anesthetic agent is selected from any, or a combination of isoflurane, propofol, halogenate gasses, ketamine, sevoflurane, desflurane, sodium pentothal, or etomidate, and other anesthetics commonly known to persons of ordinary skill in anesthesia.

In some embodiments, the anesthesia-reversing agent is administered to the subject by intravenous dose, or alternative embodiments, the anesthesia-reversing agent is administered to the subject by inhalation. In some embodiments, the anesthesia-reversing agent is administered to the subject in combination or concurrently with at least one additional therapeutic agent, such as, but not limited to a pain-reducing agent or general analgesic, such as but not limited to a opioids and other post-surgery anesthetics. In some embodiments, the pain-reducing agent or general analgesic comprises an anesthesia-reducing agent as disclosed herein, e.g., caffeine.

In some embodiments, the subject is a perioperative anesthetized patient. In some embodiments, the subject is no longer being administered an anesthesia agent, e.g., isoflurane or other anesthesia agent. In alternative embodiments, a subject can be administered the composition comprising the anesthesia-reversing agent immediately prior to cessation of administration an anesthesia agent. In such embodiments, the dose of the anesthesia agent can be reduced with an inverse relationship with the increasing dose of the anesthesia-reversing agent as disclosed herein, so that, for example, the dose of the anesthesia agent is reduced concurrently with an increase in the dose of the anesthesia-reversing agent as disclosed herein. In alternative embodiments, a subject can be administered the composition comprising the anesthesia-reversing agent subsequent to, and in some instances, immediately upon cessation of administration an anesthesia agent, such that as soon as the anesthesia agent is stopped being administered, the subject is administered at least one anesthesia-reversing agent.

In some embodiments, the dose of an anesthesia-reversing agent as disclosed herein is administered at a higher dose than ordinary and acute use of the anesthesia-reversing agent for a disease or condition, e.g., for sleep disorders or ADHD. In some embodiments, the dose of an anesthesia-reversing agent is at least about 10%, or at least about 30%, or at least about 40%, or at least about 50% or at least about 75% or at least about 2-fold or at least about 3-fold, or at least about 5-fold or higher than 5-fold higher than the ordinary use of an anesthesia-reversing agent, e.g., for the treatment of an acute disorder, disease or condition. In some embodiments, a subject can be administered a higher dose of methylphenidate than the dose used for the treatment of Attention Deficit Disorder (ADD) or Attention Deficit Hyperactivity Disorder (ADHD) in the subject. As discussed above, the dose of a methylphenidate used as an anesthesia-reversing agent according to the methods as disclosed herein, can be at least about least about 30%, or at least about 40%, or at least about 50% or at least about 75% or at least about 2-fold or at least about 3-fold, or at least about 5-fold or higher than 5-fold higher than the dose of methylphenidate used in the treatment of Attention Deficit Disorder (ADD) or Attention Deficit Hyperactivity Disorder (ADHD). In some embodiments, a dose of methylphenidate can be between about 10 mg/kg and about 5 mg/kg, and any integer between about 5 mg/kg and 10 mg/kg. In some embodiments, the dose is between about 7 mg/kg and about 0.1 mg/kg, or between about 5 mg/kg and about 0.5 mg/kg.

In some embodiments, the anesthesia-reversing agent is administered to the subject via continuous administration. In alternative embodiments, the anesthesia-reversing agent can be administered to the subject via pulse administration.

Another aspect of the present invention relates to the use of an anesthesia-reversing agent for the preparation of a medicant for reversing general anesthesia-induced unconsciousness in a subject, where the anesthesia-reversing agent can be selected from any or a combination of methylphenidate (MPH), amphetamine, modafinil, amantadine, etomidate or caffeine, according to the methods and composition as disclosed herein. In some embodiments, the medicant comprises methylphenidate which is selected from dextro-methylphenidate (D-MPH) or levo-methylphenidate (L-MPH) or a combination thereof, or an analogue or derivative thereof. In some embodiments, the medicant comprises racemic methylphenidate. In some embodiments, the medicant comprises amphetamine, which can be L-amphetamine. In some embodiments, the medicant is prepared as an intravenous medicant, and in some embodiments, the medicant is prepared as an inhalation medicant.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A shows rats inhaled isoflurane (1.5%) for a total of 45 minutes, and received normal saline or methylphenidate (5 mg/kg IV, solid arrow) five minutes before removal from the anesthetizing chamber (dashed arrow). Time to emergence was defined as the time from termination of isoflurane to return of righting (i.e. all four paws touching the floor). FIG. 1B shows a scatter plot of time to emergence for rats that received normal saline vs. methylphenidate (5 mg/kg IV). The line represents the median. ***$P<0.0001$.

FIG. 2A shows that rats which inhaled isoflurane at a dose sufficient to maintain loss of righting for a total of 40 minutes, and received normal saline. Five minutes later, methylphenidate was administered IV. Isoflurane was continued at the same dose until return of righting occurred or 30 minutes elapsed. FIG. 2B shows a dose-dependence of methylphenidate-induced emergence. FIG. 3C shows a scatter plot of time to righting for rats that received 0.5 versus 5 mg/kg IV of methylphenidate. The line represents the median. FIG. 2D shows that after pretreatment with droperidol (0.5 mg/kg IV) instead of normal saline, high-dose methylphenidate (5 mg/kg IV) did not induce return of righting in any of the six animals tested. ***posterior probability>0.95, *$P<0.05$.

FIG. 3A shows thirty-second epochs of electroencephalogram recordings from a single rat show the change from an active, theta-dominant pattern during the awake state to the delta-dominant pattern during inhalation of isoflurane (1.0%). The latter pattern is unchanged after the administration of normal saline. Administration of methylphenidate (5 mg/kg IV) induced a prompt shift in the electroencephalogram back to an active theta-dominant pattern similar to that observed during the awake state. This pattern persisted for more than 15 minutes. FIG. 3B shows thirty-second epochs of raw electroencephalogram recordings from a different animal than (FIG. 3A) show the same patterns during the awake and anesthetized states. Administration of droperidol (0.5 mg/kg IV) induced no appreciable change in the electroencephalogram pattern. However, when methylphenidate (5 mg/kg IV) was administered five minutes after droperidol, the electroencephalogram did not return to the active, theta-dominant pattern observed during the awake state. Rather, the delta-dominant pattern persisted.

FIGS. 4A-4C show spectral analysis of electroencephalogram data reveals a shift in power induced by methylphenidate that is inhibited by droperidol. Warm colors (e.g. red) represent higher power at a given frequency, while cool colors (e.g. blue) represent lower power. FIG. 4A shows a representative spectrogram computed from a rat in the awake state shows predominance of theta power (4-8 Hz). FIG. 4B shows a representative spectrogram computed from a rat inhaling isoflurane (1.0%) shows predominance of delta power (<4 Hz) before and after administration of normal saline. However, administration of methylphenidate (5 mg/kg IV) promptly induced a shift in power to an active theta-dominant pattern similar to that observed during the awake state. This animal began to move vigorously approximately 5 minutes after methylphenidate administration, generating significant motion artifacts. Therefore the experiment was promptly terminated. FIG. 4C shows a representative spectrogram computed from a rat that received droperidol (0.5 mg/kg IV) instead of normal saline shows that similar to the rat in (FIG. 4B), delta power is dominant during inhalation of isoflurane (1.0%), before and after administration of droperidol. However, after administration of droperidol, methylphenidate (5 mg/kg IV) did not induce a shift in electroencephalogram to the theta-dominant pattern characteristic of the awake state. In addition, this animal showed no purposeful movement after methylphenidate administration.

FIG. 5A shows spectrograms and power spectra computed from animals that received normal saline prior to methylphenidate (MPH). Power spectra show results of the Kolmogorov-Smirnov test for the two-minute periods before and after methylphenidate administration. At a 0.05 significance level (with Bonferonni correction) the Kolmogorov-Smirnov test rejects the null hypothesis at all frequencies except those marked with white squares. Statistically significant changes occurred at most frequencies between 0-10 Hz. (The fourth animal moved during the time window used for the analysis, and therefore motion artifact may account for the persistent high delta power observed after methylphenidate administration in this animal.) FIG. 5B shows spectrograms and power spectra computed from animals that received droperidol prior to methylphenidate (MPH). After droperidol, methylphenidate only induced statistically significant decreases in delta power.

FIG. 6A shows a time series of respiratory rate (filled circles) and tidal volume (open squares) recorded from one animal during inhalation of isoflurane (1.5%). Normal saline and methylphenidate (5 mg/kg IV) were administered at the indicated times. Methylphenidate induced a prompt and sustained increase in respiratory rate from 103 to 154 breaths per minute ($p<10-16$), while tidal volume remained essentially unchanged. FIG. 6B shows when a different animal was pretreated with droperidol (0.5 mg/kg IV) instead of normal saline, methylphenidate induced little change in respiratory rate or tidal volume.

DETAILED DESCRIPTION OF THE INVENTION

Figure 1A:
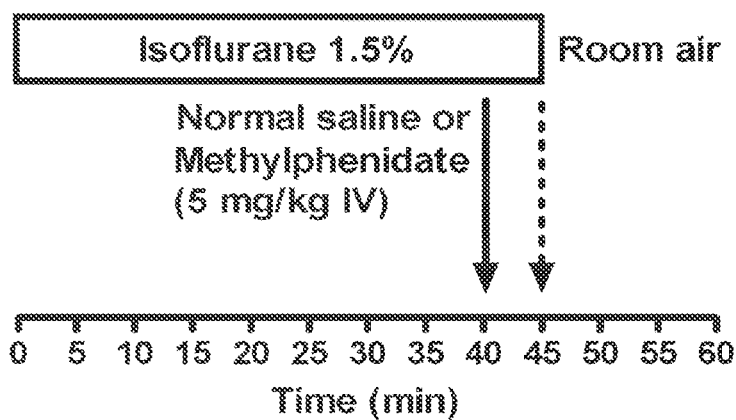
FIGS. 1A-1B show methylphenidate (MPH) decreases time to emergence from isoflurane anesthesia.

The present invention relates to compositions comprising anesthesia-reversing agents and methods of their use for facilitating emergence of a subject from anesthesia-induced unconsciousness and restoring the subject back to consciousness and cognitive function. The present invention provides several advantages, including but not limited to decreasing time required to consciousness after general anesthesia, decreased delirium after anesthesia and the like. In some embodiments, an anesthesia-reversing agent is selected from at least one or a combination of methylphenidate (MPH), amphetamine, modafinil, amantadine, caffeine, or analogues or derivatives thereof.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

The term "Amphetamine" includes dextro and levo amphetamine forms and all pharmaceutically acceptable amphetamine salts. Conversion typically involves metabolism.

The term "Methylphenidate" or "MPH" includes all methylphenidate optical isomers and all pharmaceutically acceptably methylphenidate salts. For example "methylphenidate" includes pure dexmethylphenidate (α-phenyl-2-piperidineacetatehydrochloride, (R,R')-(+)-) and racemic mixtures of d- and l-methylphenidate forms.

As used herein, a "prodrug" refers to compounds that can be converted via some chemical or physiological process (e.g., enzymatic processes and metabolic hydrolysis) to an active compound. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

The terms "amphetamine prodrug" and "methylphenidate prodrug" refer to any product that contains either an amphetamine (CAS Reg. No. 300-62-9) or methylphenidate (CAS Reg. No. 113-45-1) compound respectively conjugated to a chemical moiety such that the conjugated amphetamine or methylphenidate must undergo a conversion in a patient's body to become the active amphetamine or methylphenidate form.

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

Thus, as used herein, the term "pharmaceutically acceptable salt," is a salt formed from an acid and a basic group of a compound of the invention. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutarnate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "Pharmaceutically acceptable salts" includes derivatives of the disclosed compounds, e.g., methylphenidate (MPH), amphetamine, modafinil, amantadine, caffeine wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

The term "subject" is used interchangeably herein with "patient" and refers to a vertebrate, preferably a mammal, more preferably a primate, still more preferably a human. Mammals include, without limitation, humans, primates, wild animals, rodents, feral animals, farm animals, sports animals, and pets. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. A subject can be male or female. Mammals other than humans can be administered a composition comprising an anesthesia-reversing agent as disclosed herein, and thus, the methods and compositions described herein can be used to treat domesticated animals and/or pets.

The term "therapeutically effective amount" or "effective amount" means an amount effective, when administered to a human or non-human patient, to provide any therapeutic benefit. A therapeutic benefit may be an amelioration of symptoms, e.g., an amount effective to decrease the symptoms of binge-eating disorder or a major depressive disorder. In certain circumstances a patient may not present symptoms of a condition for which the patient is being treated. Thus a therapeutically effective amount of a compound is also an amount sufficient to provide a significant positive effect on any indicia of a disease, disorder or condition e.g. an amount sufficient to significantly reduce the frequency and severity of binge eating behavior or depressive symptoms. A significant effect on an indicia of a disorder or condition includes a statistically significant in a standard parametric test of statistical significance such as Student's T-test, where $p<0.05$; though the effect need not be significant in some embodiments. Thus, with respect to the anesthesia-reversing agents as disclosed herein, a "therapeutically effective amount" as used herein refers to an amount sufficient to effect a beneficial or desired clinical result upon treatment. Specifically, the term "therapeutically effective amount" means an amount of a an anesthesia-reversing agent as disclosed herein sufficient to measurably (i) facilitate emergence of a subject from anesthesia-induced unconsciousness or cause a measurable decrease in time from unconciousness as compared to in the absence of the anesthesia-reducing agent and/or (ii) decreased delirium on emergence of anesthesia-induced unconsciousness, and/or decrease of time to full cognitive function after anesthesia-induced unconsciousness. Therapeutically effective amounts will vary, as recognized by those skilled in the art, depending on the specific disease treated, the route of administration, the excipient selected, and the possibility of combination therapy. Other therapeutically effective amounts may vary on the subjects age, prior CNS disorders, electrolyte disturbances, temperament, surgery type and anesthesia type.

Determination of a therapeutically effective amount is well within the capability of those skilled in the art. Generally, a therapeutically effective amount can vary with the subject's history, age, condition, sex, as well as the severity, duration and type of the anesthesia used, and the medical condition in the subject, and administration of other pharmaceutically active agents. Furthermore, therapeutically effective amounts will vary, as recognized by those skilled in the art, depending on the anesthesia used, the route of administration, the excipient selected, and the possibility of combination therapy.

Physiological effects that can be measured to determine the therapeutically effective amount of an anesthesia-reducing agent to include, without limitation, time to righting (e.g., righting responses), time to emergence from anesthesia-induced unconsciousness, monitoring on an electroencephalogram to when the subject has shifted from the delta to the theta-dominant pattern of the awakened state (see Examples disclosed herein). Relevant assays to measure such effects include, without limitation, electroencephalogram, observation, spectograms, arterial blood gas and hemodynamic recordings, measurements of respiratory rate, mean arterial blood pressure and heart rate.

The term "user" refers to a subject, patient, a medical care worker, or a pharmaceutical supplier.

The term "obtaining" as in "obtaining the compound" is intended to include purchasing, synthesizing or otherwise acquiring the anesthesia-reversing agent (or indicated substance or material).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Anesthesia-Reversing Agents

As disclosed herein, one aspect of the present invention relates to compositions comprising anesthesia-reversing agents and methods of their use for facilitating emergence of a subject from anesthesia-induced unconsciousness and restoring the subject back to consciousness and cognitive function. In some embodiments, an anesthesia-reversing agent is selected from at least one or a combination of methylphenidate (MPH), amphetamine, modafinil, amantadine, caffeine, or analogues or derivatives thereof.

Methylphenidate (MPH)

One aspect of the present invention relates to use of intravenous methylphenidate (MPH, also known as RITALIN™) to rapidly reverse a subject unconscious by general anesthesia, e.g., isoflurane-induced or propofol-induced anesthesia. Methylphenidate, referred to herein as "MPH" is also known in the art as RITALIN™, is a chiral compound that exists in dextro- and levo-forms. (Sometimes referred to herein as "D-MPH" and "L-MPH", respectively, or "Dmethylphenidate" and "L-methylphenidate", respectively, but in any case, it is to be understood that each one of the terms "dextro-methylphenidate", "D-MPH", and "D-methylphenidate" are synonymous with D-threo-methylphenidate and that each one of the terms "levo-methylphenidate", "L-MPH", and "L-methylphenidate" are synonymous with L-threo-methylphenidate.) All prior work related to the post-operative arousal-promoting effects of MPH was performed with the racemic form (i.e., a 50%/50% mixture of D-MPH and L-MPH). Pure D-MPH (Focalin) is currently available in oral form for Attention Deficit Hyperactivity Disorder (ADHD), but it is not available for intravenous use. The resent inventors have now completed a study in rats to test which form of MPH (D-MPH or L-MPH) is more effective in reversing isoflurane anesthesia, using the widely accepted loss of righting reflex (LORR) to test for loss of consciousness. At an intravenous dose of 0.5 mg/kg (a typical dose of MPH reported in human studies), 83% of the rats that received D-MPH had restoration of consciousness, compared to only 33% with L-MPH.

In some embodiments, an anesthesia-reversing agents is MPH, D-MPH, L-MPH, or any pharmaceutically acceptable salt, polymorph or ester thereof.

Methylphenidate has the general chemical formula:

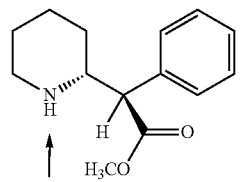

The arrow indicates a chemically accessible site at which labile groups may be added to create methylphenidate prodrugs. Amino acid methylphenidate prodrugs may be prepared via the general methods described in U.S. Pat. No. 7,105,486 (which is incorporated herein in its entirety by reference) for the preparation of amphetamine amino acid prodrugs. Amino acid methylphenidate prodrugs may comprise methylphenidate covalently bound to a single amino acid at the piperidine nitrogen or bound to a di- or tri-peptide at this position. It is also a matter of routine organic synthesis to prepare carboxamide and carbamate methylphenidate prodrugs by reacting methylphenidate with an aliphatic aldehyde or aliphatic organic acid.

Methylphenidate contains a secondary amine group and amphetamine contains an amino group both of which may be reacted to form prodrugs having a chemical moiety covalently attached to the amine or amino group of the parent drug compound. Prodrugs of amine-containing compounds have been disclosed in U.S. Patent Application No. 2007/0123468, which is hereby incorporated by reference at paragraphs [0078]-[0137] for its teaching regarding general classes of amine prodrugs, at paragraph [0140] for its teaching regarding amphetamine and methylphenidate prodrugs, at paragraphs [0176]-[0181] for its teachings of methylphenidate prodrug structures, and at paragraphs [0184]-[0189] for its teaching regarding prodrugs synthesis.

Methylphenidate possesses two centers of chirality and thus can exist as four separate optical isomers. The four isomers of methylphenidate are as follows:

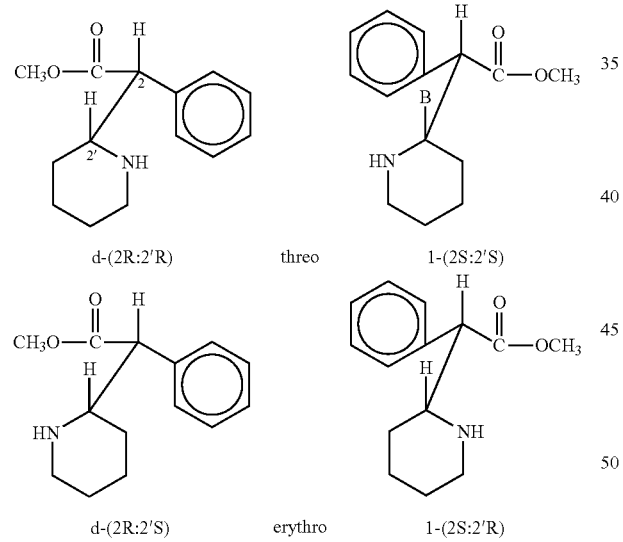

Racemic methylphenidate and its individual isomers are known. See U.S. Pat. Nos. 2,507,631, 7,164,025 and 2,957,880, which are incorporated herein in their entirety by reference, where methylphenidate can be prepared as a mixture of erythro [R*S*] and threo [R*R*] racemates, where the D-threo [or (R,R)] enantiomer has a preferred therapeutic activity. They can be prepared by conventional techniques, and can be obtained from a variety of commercial sources. Additionally, a single enantiomer of D-threo-methylphenidate or L-threo-methylphenidate can be synthesized according to the method as disclosed in U.S. Pat. No. 7,164,025 which is incorporated herein in its entirety by reference.

Diastereomers are known in the art to possess differing physical properties, such as melting point and boiling point. For example, while the threo-racemate of methylphenidate produces the desired Central Nervous System action, the erythro-racemate contributes to hypertensive side effects and exhibits lethality in rats.

Additional studies in animals, children and adults have demonstrated pharmacological activity in the d-threo isomer of methylphenidate (2R:2'R). See Patrick et al., J. Pharmacol. & Exp. Therap., 241:152-158 (1987). The role of the 1-isomer in toxicity or adverse side effects has not been thoroughly examined.

Although 1-threo-methylphenidate is rapidly and stereoselectively metabolized upon oral administration, intravenous administration or inhalation results in high 1-threo-methylphenidate serum levels. Srinivas et al., Pharmacol. Res., 10:14-21 (1993). Accordingly, in some embodiments, one can use the d-threo isomer (2R:2'R) of methylphenidate as an analgesic-reversing agent as disclosed herein, which is substantially free of the 1-threo isomer, and produces a methylphenidate medication which retains high activity levels and simultaneously possesses reduced euphoric effect and reduced potential for abuse among patients.

The 2R:2'R isomer of methylphenidate has the following structure and is disclosed in U.S. Pat. No. 5,908,850 which is incorporated herein in its entirety by reference.

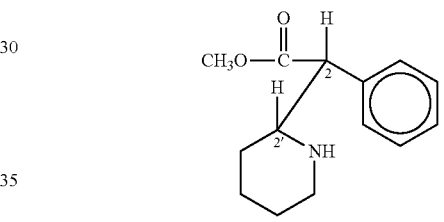

2R:2'R isomer of methylphenidate

U.S. Pat. No. 2,507,631, to Hartmann et al. describes methylphenidate and processes for making the same. U.S. Pat. No. 2,957,880, to Rometsch et al. describes the conversion of .alpha.-aryl-.alpha.-piperidyl-(2)-acetic acids and derivatives thereof (including methylphenidate) into their respective racemates. Holmes et al., J. Clin. Psychiatry, 50:5-8 (1989) reported on the use of racemic methylphenidate (RITALIN™) and dextroamphetamines in the treatment of cognitive impairment in AIDS patients. Srinivas et al., J. Pharmacol. & Exp. Therap., 241:300-306 (1987) described use of racemic dl-threo-methylphenidate (RITALIN™) in the treatment of ADD in children. This study reported a 5-fold increase in plasma levels of d-threo-methylphenidate in children treated with racemic methylphenidate, but was otherwise inconclusive with regard to the efficacy of a single methylphenidate isomer at therapeutically significant doses. Srinivas et al., Clin. Pharmacol. Ther., 52:561-568 (1992) studied the administration of dl-threo, d-threo and 1-threo-methylphenidate to children suffering from ADHD. While Srinivas et al. reported the pharmacodynamic activity of dl-threo-methylphenidate resides in the d-threo isomer, this study investigated neither the adverse side effects of the 1-threo isomer, nor the euphoric effects of the single isomers or racemate. Single isomer dosages below ½ of the racemate dosage were not studied. Patrick et al., J. Pharmacol. & Exp. Therap., 241:152-158 (1986) examined the pharmacology of the enantiomers of threo-methylphenidate, and assessed the relative contribution of each isomer to central and peripheral actions of RITALIN™. Brown, G., Intl. J. Psych. Med., 25(1):21-37 (1995) reported the use of racemic methylphenidate for the treatment of AIDS cognitive decline. Patrick et al., Psychopharmacology: The Third Generation of Progress, Raven Press, N.Y. (1987) examined the pharmacokinetics and actions of methylphenidate in the treatment of Attention Deficit Hyperactivity Disorder (ADHD). Patrick noted the d-threo isomer possesses higher activity than the 1-threo isomer, and that d-threo methylphenidate may be responsible for the therapeutic activity in the racemic drug. Aoyama et al., Clin. Pharmacol. Ther., 55:270-276 (1994) reported on the use of (+)-threo-methylphenidate in the treatment of hypersomnia. Aoyama et al. describe a correlation between sleep latency in patients and plasma concentration or (+)-threo-methylphenidate. The U.S. patents and patent applications are incorporated herein in their entirety by reference.

MPH Analogues

Methylphenidate analogs are compounds have a structure highly similar to methylphenidate, and like methylphenidate bind to the brain dopamine transporter and affect the reuptake of dopamine in the brain, but which have an extended duration of action relative to methylphenidate. Methylphenidate analogs include compounds having the general formula:

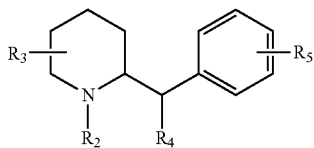

where at least one of $R_2$ and $R_4$ is a non-hydrogen substituent differing from the group that occurs at the corresponding position in methylphenidate and R1 and R5 are independently chosen from hydrogen, halogen, hydroxyl, $C_1$-$C_2$ alkyl, and $C_1$-$C_2$ alkoxy, and the like. Methylphenidate analogs have been disclosed in U.S. Non-provisional Patent Application No. 2006/0100243, which is hereby incorporated by reference at paragraphs [0007]-[0021] for its teachings regarding the methylphenidate analog structures, at paragraphs [0055]-[0063] for its teachings regarding the methylphenidate analog structure and synthesis, and at paragraphs [0083]-[0085] for its exemplary synthesis of methylphenidate analogs.

In some embodiments, intravenous D-MPH can be administered to a subject upon completion of surgery as a highly effective and safe way to rapidly reverse general anesthesia. Accordingly, this approach could lead to improved patient safety and operating room efficiency. It is to be understood, however, that the present invention is not limited to using D-MPH alone as the agent which reverses general anesthesia. In some embodiments, L-MPH alone may be used as an anesthesia-reversing agent as disclosed herein, or a mixture of D-MPH and L-MPH may be used as such anesthesia-reversing agent, and therefore, a composition comprising more than one "anesthesia-reversing agent" can be used to reverse general anesthesia, for example, a composition can comprise D-MPH and L-MPH. In some embodiments, a composition comprises equal or substantially equal parts of D-MPH and L-MPH (i.e., exactly or about 50% D-MPH and exactly or about 50% L-MPH). In some embodiments, racemic MPH is used. It is to be understood, however, that in some embodiments, D-MPH and L-MPH alternatively may be present in a composition mixture in unequal or substantially unequal parts; therefore, the D-MPH may be present in any amount and the L-MPH may be present in any amount. Further, one of ordinary skill in the art will recognize that a composition comprising D-MPH and L-MPH optionally may include one or more compounds or anesthesia-reversing agents as disclosed herein other than D-MPH and L-MPH, and each one of these one or more compounds may or may not act to reverse the state of general anesthesia.

There are no drugs currently available for reversal of general anesthesia at the end of surgery. The safety profile of D-MPH is now well known and has been established in adults as well as in children, for whom it is the primary therapy for treating ADHD. Also well understood now are its mechanisms of action in the brain which entail blocking of monoaminergic transport systems, thereby increasing the brain levels of the arousal neurotransmitters dopamine, norepinephrine and histamine. At present, there is no medical indication for intravenous use of D-MPH. Therefore, one aspect of the present invention relates to the use of intravenous D-MPH and/or L-MPH to actively reverse the state of general anesthesia.

In some embodiments, a composition comprising D-MPH and/or L-MPH can be widely used in subjects to rapidly reverse general anesthesia at the end of surgery. In addition, D-MPH may find use as a "rescue" drug in patients who are accidentally oversedated and become unresponsive or apneic during conscious sedation.

The effective dose of methylphenidate, including D-methylphenidate alone, L-methylphenidate alone, or a mixture of those two, is selectable and variable. For example, the dose may be about 0.5 mg/kg of patient weight. Further, restoration of mobility or consciousness in an anesthetized patient who has been exposed to an effective dose methylphenidate, including D-methylphenidate alone, Lmethylphenidate alone, or a mixture of those two, may occur quickly. For example, such restoration of mobility or consciousness may occur in as little as about 5 minutes or about 10 minutes.

Amphetamine and Amphetamine Analogues

One aspect of the present invention relates to use of Amphetamine as an anesthesia-reversing agent according to the compositions and methods as disclosed herein to rapidly reverse a subject's unconsciousness by general anesthesia, e.g., isoflurane-induced or propofol-induced anesthesia or other anesthesia's, for example etimidate. In some embodiments, amphetamine is dextro-amphetamine (D-amphetamine) or any pharmaceutically acceptable salts, polymorphs or esters thereof. In some embodiments, amphetamine is levo-amphetamine (L-amphetamine) or any pharmaceutically acceptable salts, polymorphs or esters thereof.

Amphetamine has the Chemical Formula:

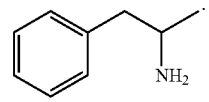

Amphetamine prodrugs, and methods of preparing amphetamine prodrugs have been described previously. U.S. Pat. No. 7,105,486, which describes the preparation of lisdexamfetamine, is hereby incorporated by reference at cols. 20 to 22 for its teachings regarding the synthesis of amino acid amphetamine prodrugs. In addition to amino acid prodrugs it is possible to prepare a number of other amphetamine prodrugs by reacting the amphetamine amino group with a chemically labile moiety. It is within the ability of those of ordinary skill in the art of chemical synthesis to prepare carboxamide amphetamine prodrugs by reacting amphetamine with an aliphatic aldehyde and to prepare carbamate amphetamine prodrugs by reacting amphetamine with an aliphatic organic acid.

Lisdexamfetamine dimesylate, CAS Reg. No. 608137-32-3, (2S)-2,6-diamino-N-[(1S)-1-methyl-2-phenylethyl] hexanamide dimethanesulfonate, is an amphetamine prodrug in which L-lysine is covalently bound to d-amphetamine. Lisdexamfetamine dimesylate is sold under the trade name VYVANSE (Shire). It has the chemical formula:

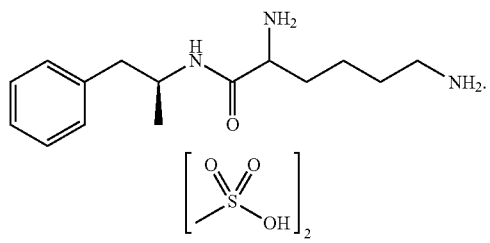

"Lisdexamfetamine" is typically administered as a dimesylate salt but includes all pharmaceutically acceptable salts of lisdexamfetamine free base. The term "lisdexamfetamine" also encompasses any pharmaceutically acceptable salt, polymorph or ester thereof.

In some embodiments, amphetamine, amphetamine analogues or prodrugs thereof can be used as an anesthetic-reversing agent as disclosed herein at a dose of about at least about 0.1 mg/kg, or about 0.2 mg/kg, or about 0.3 mg/kg, or about 0.4 mg/kg, or about 0.5 mg/kg, or about 0.6 mg/kg, or about 0.7 mg/kg, or about 0.8 mg/kg or about 0.9 mg/kg, or about 1 mg/kg, or about 2 mg/kg or about 3 mg/kg or 4 mg/kg or 5 mg/kg or about 6 mg/kg or about 7 mg/kg or about 8 mg/kg or about 9 mg/kg or about 10 mg/kg, or greater than about 10 mg/kg. In some embodiments, amphetamine, amphetamine analogues or prodrugs thereof can be used as an anesthetic-reversing agent as disclosed herein at a dose of about 0.5 mg/kg. In some embodiments, amphetamine, amphetamine analogues or prodrugs thereof can be used as an anesthetic-reversing agent as disclosed herein at a dose of between 0.1 mg/kg to 0.5 mg/kg, or about 0.5-1 mg/kg, or about 1-2 mg/kg or about 2-3 mg/kg, or about 2-5 mg/kg or about 5-10 mg/kg, or about 0.05-5 mg/kg or any integer between 0.5 mg/kg and about 10 mg/kg.

Modafinil or any Pharmaceutically Acceptable Salts, Polymorphs or Esters Thereof One aspect of the present invention relates to use of modafinil as an anesthesia-reversing agent according to the compositions and methods as disclosed herein to rapidly reverse a subject's unconsciousness by general anesthesia, e.g., inhalation anesthesia such as, but not limited to isoflurane-induced or propofol-induced anesthesia or etomidate-induced anesthesia.

Modafinil is also known by the names PROVIGIL™, ALERTEC™, MODAVIGIL™ MODALERT™, MODIODAL™, MODAFINILO™, CARINA™, VIGIA™, and is an analeptic drug manufactured by Cephalon, and is approved by the U.S. Food and Drug Administration (FDA) for the treatment of narcolepsy, shift work sleep disorder, and excessive daytime sleepiness associated with obstructive sleep apnea.

Modafinil compound is 2-[(diphenylmethyl)sulfinyl]acetamide and can be synthesized by the method as described in U.S. Pat. No. 4,927,855, which is incorporated herein by reference, and has the following chemical formula:

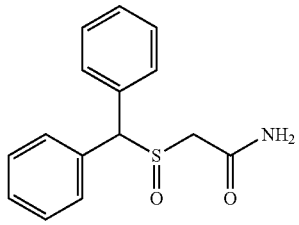 [SMILES: NC(=O)CS(=O)C(c1ccccc1)c1ccccc1]

In some embodiments, Modafinil used in the methods and compositions as disclosed herein as an anesthesia-reversing agent is an acetamide derivative modafinil, which is 2-(benzhydrylsulfinyl)acetamide and is also known as 2-[(diphenylmethyl)sulfinyl]acetamide. In some embodiments, Modafinil polymeric forms can be used, such as those disclosed in U.S. Pat. Nos. 7,649,020; 7,405,323; 6,992,219, as well as enantiomers, analogues and derivatives can be used which are disclosed in U.S. Pat. Nos. 7,704,975; 7,779,540; 7,576,133; 7,566,805; 7,541,493; 7,368,591; 7,317,126; 7,316,918; 7,297,346; 7,235,691; 7,229,644; 7,141,555; 7,115,281; 7,087,647; 7,057,068; 6,489,363; 6,348,500; 6,346,548; 5,612,379; 5,401,776, each of which are incorporated herein in their entirety by reference.

In some embodiments, modafinil can be used as an anesthetic-reversing agent as disclosed herein at a dose of about at least about 1 mg/kg, or about 2 mg/kg or about 3 mg/kg or 4 mg/kg or 5 mg/kg or about 10 mg/kg or about 20 mg/kg or greater than about 20 mg/kg. In some embodiments, modafinil can be used as an anesthetic-reversing agent as disclosed herein at a dose of about 5 mg/kg or about 10 mg/kg. In some embodiments, modafinil can be used as an anesthetic-reversing agent as disclosed herein at a dose of between 0.5 mg/kg and 1 mg/kg, or about 1-2 mg/kg or about 2-3 mg/kg, or about 2-5 mg/kg or about 5-10 mg/kg, or about 10-20 mg/kg or about 0.025-0.5 mg/kg or any integer between 0.025 mg/kg and about 20 mg/kg.

Amantadine or any Pharmaceutically Acceptable Salts, Polymorphs or Esters Thereof One aspect of the present invention relates to use of amantadine as an anesthesia-reversing agent according to the compositions and methods as disclosed herein to rapidly reverse a subject's unconsciousness by general anesthesia, e.g., inhalation anesthesia such as, but not limited to isoflurane-induced or propofol-induced anesthesia or etomidate-induced anesthesia.

Amantadine is the organic compound known formally as 1-adamantylamine or 1-aminoadamantane. The molecule consists of adamantane backbone that has an amino group substituted at one of the four methyne positions. This pharmaceutical is sold under the name SYMMETREL™ for use both as an antiviral and an antiparkinsonian drug. Rimantadine is a closely-related derivative of adamantane with similar biological properties. Amantadine has the following chemical formula:

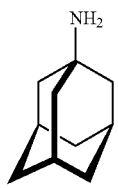

Extended release forms of amantadine have been described in the art. U.S. Pat. No. 5,358,721, to Guittard et al., and U.S. Pat. No. 6,217,905, to Edgren et al., which are incorporated herein in their entirety by reference, and each disclose an oral osmotic dosage form comprising an antiviral or anti-Parkinson's drug, respectively, where in each case amantadine is listed as a possible drug to be utilized in the dosage form. U.S. Pat. No. 6,194,000, to Smith et al., incorporated herein in their entirety by reference, discloses analgesic immediate and controlled release pharmaceutical compositions utilizing NMDA receptor antagonists, such as amantadine, as the active agent. U.S. Patent Appl. Publication Nos. US 2006/0252788, US 2006/0189694, US 2006/0142398, and US 2008/0227743, incorporated herein in their entirety by reference, all to Went et al., each disclose the administration of an NMDA receptor antagonist, such as amantadine, optionally in controlled release form. U.S. Patent application US 2011/0189273 also incorporated herein in its entirety by reference, discloses alternative formulations of amantidine.

In some embodiments, amantadine is amantadine hydrochloride is designated chemically as 1-adamantanamine hydrochloride or the chemical structure:

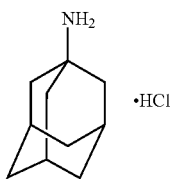 [SMILES: NC12CC3CC(CC(C3)C1)C2 ; Cl]

Amantadine hydrochloride is a stable white or nearly white crystalline powder freely soluble in water and soluble in alcohol and in chloroform. Amantadine hydrochloride has pharmacological actions as both an anti-Parkinson and an antiviral drug. In some embodiments, Amantadine can be used as an anesthetic-reversing agent as disclosed herein at a dose of about at least about 1 mg/kg, or about 2 mg/kg or about 3 mg/kg or 4 mg/kg or 5 mg/kg or greater than 5 mg/kg. In some embodiments, Amantadine can be used as an anesthetic-reversing agent as disclosed herein at a dose of about 3 mg/kg. In some embodiments, Amantadine can be used as an anesthetic-reversing agent as disclosed herein at a dose of between 0.5 mg/kg and 1 mg/kg, or about 1-2 mg/kg or about 2-3 mg/kg, or about 2-5 mg/kg or about 0.025-0.5 mg/kg or any integer between 0.025 mg/kg and about 10 mg/kg.

Caffeine or any Pharmaceutically Acceptable Salts, Polymorphs or Esters Thereof

One aspect of the present invention relates to use of caffeine as an anesthesia-reversing agent according to the compositions and methods as disclosed herein to rapidly reverse a subject's unconsciousness by general anesthesia, e.g., inhalation anesthesia such as, but not limited to isoflurane-induced or propofol-induced anesthesia or etomidate-induced anesthesia.

Caffeine, or 3,7-dihydro-1,3,7-trimethyl-1H-purine-2,6-dione, has the structural formula as shown below. This substance has been used alone, intravenously, in the treatment of headaches and has also been used in combination with selected drugs. Caffeine has the following structure:

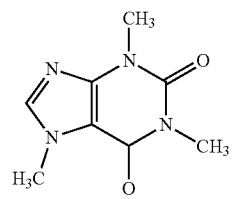

Caffeine is a methylxanthines, and caffeine for use as an anesthesia-reversing agent can be obtained and delivered (e.g., via inhalation routes or aqueous dosage forms or oral spray forms, nasal delivery methods) according to the methods as disclosed in U.S. Pat. Nos. 7,560,465; 7,448,469; 5,900,416; 5,700,484; 5,502,056; 5,456,677; 7,488,469; 7,560,465; 7,078,016; 4,778,810; 4,486,436 each of which are incorporated herein in their entirety by reference.

In some embodiments, caffeine can be used as an anesthetic-reversing agent as disclosed herein at a dose of about at least about 1 mg/kg, or about 2 mg/kg or about 3 mg/kg or 4 mg/kg or 5 mg/kg or about 6 mg/kg or about 7 mg/kg or about 8 mg/kg or about 9 mg/kg or about 10 mg/kg, or greater than about 10 mg/kg. In some embodiments, caffeine can be used as an anesthetic-reversing agent as disclosed herein at a dose of about 5 mg/kg. In some embodiments, caffeine can be used as an anesthetic-reversing agent as disclosed herein at a dose of between 0.5 mg/kg and 1 mg/kg, or about 1-2 mg/kg or about 2-3 mg/kg, or about 2-5 mg/kg or about 5-10 mg/kg, or about 0.05-5 mg/kg or any integer between 0.5 mg/kg and about 10 mg/kg.

Anesthesia-Reversing Agents

In particular, the present invention generally relates to increasing the time to consciousness after withdrawal of anesthesia using a composition comprising at least one anesthesia-reversing agent as disclosed herein, wherein the anesthesia-reversing agent is selected from the group comprising; methylphenidate (MPH), amphetamine, modafinil, amantadine, caffeine, or analogues or derivatives thereof.

In some embodiments, an anesthesia-reversing agent is MPH, e.g., D-MPH or any pharmaceutically acceptable salt, polymorph or ester thereof.

In some embodiments, a composition comprising at least one anesthesia-reversing agent as disclosed herein is administered in an effective amount to facilitate emergence of general anesthesia-induced unconsciousness in a subject, or decrease the time to cognitive function after general anesthesia of a subject by a statistically significant increase as compared to in the absence of an anesthesia-reversing agent. In some embodiments, a composition comprising at least one anesthesia-reversing agent as disclosed herein is administered to an unconscious subject intravenously almost immediately after administration of the general anesthesia is removed or stopped, to decrease the time to consciousness by a statistically significant increase as compared to in the presence of a control agent, such as, for example, physotigamine (PHY).

In some embodiments, a composition comprising at least one anesthesia-reversing agent as disclosed herein, for example, any one, or any combination of a methylphenidate (MPH), amphetamine, modafinil, amantadine, caffeine, or analogues or derivatives thereof, or in particular, D-MPH is administered in an effective amount to a subject to reduce the time to consciousness (e.g., time to awakening) by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to the time for passive awakening from general anesthesia-induced unconsciousness, or compared to awakening from general anesthesia-induced unconsciousness in the presence of a negative control agent, such PHY.

In some embodiments, a composition comprising at least one anesthesia-reversing agent as disclosed herein, for example, any one, or any combination of a methylphenidate (MPH), amphetamine, modafinil, amantadine, caffeine, or analogues or derivatives thereof, or in particular, D-MPH is administered in an effective amount to a subject so that the subject awakens or emerges from general-anesthesia induced unconsciousness earlier (or faster) by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to the time required for passive awakening from general anesthesia-induced unconsciousness, or compared to awakening from general anesthesia-induced unconsciousness in the presence of a negative control agent, such PHY.

In some embodiments, a composition comprising at least one anesthesia-reversing agent as disclosed herein, for example, any one, or any combination of a methylphenidate (MPH), amphetamine, modafinil, amantadine, caffeine, or analogues or derivatives thereof, or in particular, D-MPH is administered in an effective amount to a subject to reduce symptoms of delirium on awakening or emergence from general-anesthesia induced unconsciousness by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to the delirium symptoms experienced by subject on passive awakening from general anesthesia-induced unconsciousness, or compared to awakening from general anesthesia-induced unconsciousness in the presence of a negative control agent, such PHY. The reduced delirium by the compositions and methods as disclosed herein can be emergence delirium and hypoactive emergence delirium, which are well know by persons of ordinary skill in the art, and are described in Radtke et al., Minerva Anestesiol. 2010; 76(6):394-403. Delirium is disturbance of consciousness, and a change in cognition or a perception of a mental dissociation that can include hallucinations, psychimotor agitation and delusions, and can include restlessness, incoherence, irritability, screaming and involuntary activity, as well as belligerent behavior and disorientation. Delerium can be quantitated using the Riker sedation-agitated scale (Lepouse et al., Emergence Delirium In Adults in the Post-Anesthesia Care Unit, J. Anesthesia, 2006; 96; 747-753), and includes assessment of eye contact, purposeful actions, awareness of surroundings, restlessness and inconsolability and the like.

In some embodiments, a subject is a mammal. In certain embodiments, a mammal is an animal. In certain embodiments, the mammal is a human. In some embodiments, the human is a child. In certain embodiments, a human is under the age of 18. In some embodiments, a human is under the age of 10. In some embodiments, a human is under the age of 2. In some embodiments, an animal is a domesticated animal, including but not limited to, dog, cat, horse, cattle and the like.

In some embodiments, provided herein are methods for increasing the amount of consciousness or mental cognitive functioning of an unconscious subject wherein the subject is unconscious by general anesthesia, comprising administering to the subject a composition comprising one or more anesthesia-reversing agent selected from the group comprising; methylphenidate (MPH), amphetamine, modafinil, amantadine, caffeine, or analogues or derivatives thereof, as the free acid, a pharmaceutically acceptable salt, or ester thereof.

In some embodiments, the anesthesia-reversing agent is administered to the subject after administration of the general anesthesia, and in some embodiments, the anesthesia-reversing agent is administered in the last 10% of the surgery, concurrent with the administration of the general anesthesia. In such latter embodiments, it is envisioned that the dose of the general anesthesia is reduced as the dose of the anesthesia-reversing agent is increased, such that there is an inverse relationship between the dose of the general anesthesia and the dose of the anesthesia-reversing agent.

In some embodiments, the methods for emerging a subject from general anesthesia-induced-unconsciousness further comprises administering to the subject at least one other therapeutic agent with at least one other anesthesia reversing agent, wherein the therapeutic agent can be selected from the group consisting of; analgesic, pain medication, anti-inflammatory agent and the like.

In one embodiment, the invention relates to compositions and methods useful in the treatment and prevention of delirium occurring during emergence of general-anesthesia-induced unconsciousness. Delirium as used herein refers to a disturbance of consciousness, and a change in cognition or a perception of the subject as they awaken from general anesthesia-induced unconsciousness that can include hallucinations, psychomotor agitation and delusions, and can include restlessness, incoherence, irritability, screaming and involuntary activity, as well as belligerent behavior and disorientation. Delerium can be quantitated using the Riker sedation-agitated scale (Lepouse et al., Emergence Delirium In Adults in the Post-Anesthesia Care Unit, J. Anesthesia, 2006; 96; 747-753), and includes assessment of eye contact, purposeful actions, awareness of surroundings, restlessness and inconsolability and the like. Delerium can be measured by one of ordinary skill in the art by the Riker sedation-agitated scale.

Without wishing to be bound by theory, emergence delirium (ED) is also referred to in the art as emergence agitation (EA), and is a well documented phenomenon occurring in children and adults in the immediate postoperative period. Delirium is disturbance of consciousness, and a change in cognition or a perception of a mental dissociation that can include hallucinations, psychomotor agitation and delusions, and can include restlessness, incoherence, irritability, screaming and involuntary activity, as well as belligerent behavior and disorientation. Delerium can be quantitated using the Riker sedation-agitated scale (Lepouse et al., Emergence Delirium In Adults in the Post-Anesthesia Care Unit, J. Anesthesia, 2006; 96; 747-753), and includes assessment of eye contact, purposeful actions, awareness of surroundings, restlessness and inconsolability and the like. In children, emergence delirium is defined as a dissociated state of consciousness in which the child is inconsolable, irritable, uncompromising or uncooperative, typically thrashing, crying, moaning, or incoherent. Additionally paranoid ideation has been observed in combination with these emergence behaviors. Characteristically these children do not recognize or identify familiar and known objects or people. Parents who witness this state claim the behavior is unusual and uncustomary for the child. Although generally self limiting (5-15 min) ED can be severe and may result in physical harm to the child and particularly the site of surgery.

Signs and symptoms of emergence delirium or agitation after anesthesia include excitement and alternating periods of lethargy followed by excitement and disorientation. Inappropriate behavior such as screaming, kicking, and use of profanities also may occur. Also, the patients generally do not respond appropriately to commands.

Emergence delirium can occur after most inhalational agents, e.g., inhalation anesthesia agents desflurane and sevoflurane and intravenous agents including midazolam, remifentanil and propofol. Other drugs know to be associated with ED include 1) atropine or scopolamine, 2) ketamine, 3) droperidol, 4) barbiturates and possibly, 5) benzodiazepines.

Physiological causes of emergence delirium include, but are not limited to, age, Hypoxemia, Hypercapnia, Hyponatremia, Hypoglycemia, Intracranial injury, Sepsis, Alcohol withdrawal, Airway obstruction, Gastric dilatation, Full bladder, Pain, Hypothermia, Sensory overload, and Sensory deprivation and electrolyte disturbances. Pharmacological causes of emergence delirium include, but are not limited to rapid emergence, Ketamine, Droperidol, Benzodiazepines, Metoclopramide, Atropine, Scopolamine, volitle anestheics, raglan, central anticholinergic syndrome, neuroleptics, digoxin, beta-blockers, steroids, anticonvulsants, oral hypoglycemics.

Risk factors for emergence delirium are well known, and include, without limitation, age, (e.g., ages 2-5 are most vulnerable), underlying medical condition, medication, CNS disorders, electrolyte disturbances, temperament, surgery type and anesthesia type. Adverse effects of ED: risk of injury to patient and staff, worry of permanent neurological sequelae, disruptive to the post-anesthesia care unit, displeasure of the subject, family and staff with the whole operative experience Administration In some embodiments, compositions comprising at least one or any combination of anesthesia-reversing agent selected from the group comprising; methylphenidate (MPH), amphetamine, modafinil, amantadine, caffeine, or analogues or derivatives thereof, in particular D-MPH which can be directly or indirectly administered to the patient. Indirect administration can also be performed, for example, by administering to the subject a pro-drug of the anesthesia-reversing agent and subsequently introducing to the subject an activator of the prodrug to release the activated functional anesthesia-reversing agent to the patient.

Direct administration of compositions comprising at least one or any combination of anesthesia-reversing agent selected from the group comprising; methylphenidate (MPH), amphetamine, modafinil, amantadine, caffeine, or analogues or derivatives thereof, can also be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

In some embodiments, the anesthesia-reversing agent selected from the group comprising; methylphenidate (MPH), amphetamine, modafinil, amantadine, caffeine, or analogues or derivatives thereof, is administered via intravenous administration.

In some embodiments, a composition comprising at least one or any combination of anesthesia-reversing agent selected from the group comprising; methylphenidate (MPH), amphetamine, modafinil, amantadine, caffeine, or analogues or derivatives thereof can be administered by transdermal transfusion such as with a dermal or cutaneous patch, by direct contact with a particular tissue, for example, bone marrow through an incision or some other artificial opening into the body.

In some embodiments, compositions may also be administered by inhalation, e.g., via a aerosol administration or to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, or injectable forms of administration. Compositions may be administered as a bolus injection or spray, can in some embodiments can be administered as a bolus injection immediately after surgery and then sequentially over time (episodically) such as every two, four, six or eight hours, every day (QD) or every other day (QOD), or over longer periods of time such as weeks to months. In some embodiments, compositions comprising an anesthesia-reversing agent can also be administered in a timed-release fashion such as by using slow-release resins and other timed or delayed release materials and devices.

Orally active compositions comprising at least one or any combination of anesthesia-reversing agent selected from the group comprising; methylphenidate (MPH), amphetamine, modafinil, amantadine, caffeine, or analogues or derivatives thereof, in D-MPH are more preferred as oral administration is usually the safest, most convenient and economical mode of drug delivery. Oral administration is usually disadvantageous because compositions are poorly absorbed through the gastrointestinal lining Compounds which are poorly absorbed tend to be highly polar. Consequently, the anesthesia-reversing agents as described herein can be made orally bioavailable by reducing or eliminating their polarity. This can often be accomplished by formulating a composition with a complimentary reagent which neutralizes its polarity, or by modifying the compound with a neutralizing chemical group. Oral bioavailability is also a problem because drugs are exposed to the extremes of gastric pH and gastric enzymes. These problems can be overcome in a similar manner by modifying the molecular structure to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the subject may be therapeutic or prophylactic. Both prophylactic and therapeutic uses are readily acceptable because these compounds are generally safe and non-toxic. In some embodiments, prophylactic treatments involve administration of a composition comprising an anesthesia-reversing agent selected from the group comprising; methylphenidate (MPH), amphetamine, modafinil, amantadine, caffeine, or analogues or derivatives thereof to reverse general anesthesia in a subject when unconsciousness is no longer desired and to prevent the delirium on awakening from anesthesia-induced unconsciousness. This is particularly useful for all subjects, as emergence delirium is a serious clinical problem with an incidence of as high as 30% in pediatric patients undergoing general anesthesia.

Prophylactic treatment is also useful when the subject has prior incidence of delirium on emergence from general anesthesia-induced unconsciousness, or is a subject suspected to experience delirium on emergence from general anesthesia-induced unconsciousness without having any prior delirium symptoms on anesthesia. For example, otherwise healthy patients who have at least one or more of the characteristics of risk of delirium can be administered a composition comprising at least one anesthesia-reversing agent as disclosed herein prophylactically. Subjects at risk of delirium include any subject undergoing general anesthesia with one or more of the following, between 2-7 years of age, Hypoxemia, Hypercapnia, Hyponatremia, Hypoglycemia, Intracranial injury, Sepsis, Alcohol withdrawal, Airway obstruction, Gastric dilatation, Full bladder, Pain, Hypothermia, Sensory overload, and Sensory deprivation and electrolyte disturbances. Subjects at risk of delirium also include any subject undergoing general anesthesia currently one or more medications such as, Ketamine, Droperidol, Benzodiazepines, Metoclopramide, Atropine, Scopolamine, volatile anesthetics, raglan, central anticholinergic syndrome, neuroleptics, digoxin, beta-blockers, steroids, anticonvulsants, oral hypoglycemics. Subjects at risk of delirium on emergence of general-anesthesia-induced unconsciousness without limitation, age, (e.g., ages 2-5 are most vulnerable), underlying medical condition, medication, CNS disorders, electrolyte disturbances, temperament, surgery type and anesthesia type.

In some embodiments, therapeutic treatment involves administration of one or more anesthesia-reversing agent as disclosed herein to a subject suffering from one or more symptoms of the anesthesia-induced delirium upon awakening. Symptoms of delirium are commonly known to ordinary surgery practitioners (physicians, nurses, anesthesia physicians and technicians) and typically include, for example, inconsolable, irritable, uncompromising or uncooperative, typically thrashing, crying, moaning, incoherent, paranoid, inability to recognize or identify familiar or known objects or people, excitement and alternating periods of lethargy followed by excitement and disorientation, as well as inappropriate behavior such as screaming, kicking, and use of profanities also may occur. The present invention of administering anesthesia-reversing agents provides relief and even partial relief from one or more of these symptoms. Further, treatments that alleviate a pathological symptom can allow for other treatments to be administered.

In some embodiments, therapeutic treatment of a subject with an anesthesia-reversing agent as disclosed herein can be administered to an unconscious subject whom are inadvertently or accidently oversedated. In some embodiments, therapeutic treatment of a subject with an anesthesia-reversing agent as disclosed herein can be used for a subject whom has become unresponsive or apnic during conscious sedation as a result of the general anesthesia.

In some embodiments, composition comprising an anesthesia-reversing agent selected from the group comprising; methylphenidate (MPH), amphetamine, modafinil, amantadine, caffeine, or analogues or derivatives thereof as disclosed herein can be used in combination with other antidelirium agents or therapies to maximize the effect of the compositions in an additive or synergistic manner. Antidelirium agents include, without limitation, midazolam, benzodizepines, dexmedetomidine and clonidine, opiods and other agents. Combinations of therapies may also be effective in any one of an additive, logarithmic, or synergistic, and methods involving combinations of therapies may be simultaneous protocols, intermittent protocols or protocols which are empirically determined.

Doses and Administration:

In some embodiments, a composition comprising an anesthesia-reversing agent selected from the group comprising; methylphenidate (MPH), amphetamine, modafinil, amantadine, caffeine, or analogues or derivatives thereof can be administered to the subject by pulsed administration which can be more effective than continuous treatment because total pulsed doses are often lower than would be expected from continuous administration of the same composition. Each pulse dose can be reduced and the total amount of drug administered over the course of treatment is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient amount of an anesthesia-reversing agent available for the required period of time for effective awakening after anthestisa-induced unconsciousness. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients.

Individual pulses of a composition comprising an anesthesia-reversing agent selected from the group comprising; methylphenidate (MPH), amphetamine, modafinil, amantadine, caffeine, or analogues or derivatives thereof as disclosed herein can be delivered to the patient continuously over a period of several minutes, such as about 2-10, 10-15, 15-20, 20-25, 25-30, 30-40, 40-50 or 50-60 minutes, or several hours, such as 1-2, 3, 4, 5, 6, 7, 8-10, or 10-12 hours, preferably from about 30 minutes to about 12 hours and more preferably from about 30 minutes to about 2 hours. Alternatively, periodic doses can be administered in a single bolus or a small number of injections of the composition over a short period of time, typically less than 1 or 2 hours. In certain instances, a subject can stop receiving the pulses of a composition comprising an anesthesia-reversing agent when the subject is substantially awake and is mobile following general anesthesia-induced unconsciousness, such that there are positive consequences that raise the patient's standard of post-operative care such as, for example, increased activity or mobility, fewer anesthesia related side-effects, quicker hospital stay post-surgery etc.

The interval between pulses or the interval of no delivery is greater than 12 hours, and can be shorter, e.g., every 10 minutes, or every 15 minutes, or every 30 minutes till the subject is fully conscious after general-anesthesia induced unconsciousness. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives, intervals may be 25, 50, 100, 150, 200, 250 300 and even 500 times the half life of the chemical composition. The number of pulses in a single therapeutic regimen may be as little as two, but is typically from about 5 to 10, 10 to 20, 15 to 30 or more. In some embodiments, patients receive the anesthesia-reversing agent till the subject is fully conscious and mobile and cognitive function restored according to the methods of this invention without the problems (e.g., delirium) and inconveniences associated with emergence or awakening from general anesthesia-induced unconsciousness passively or without an anesthesia-reversing agent as disclosed herein.

In certain embodiments, a composition comprising an anesthesia-reversing agent selected from the group comprising; methylphenidate (MPH), amphetamine, modafinil, amantadine, caffeine, or analogues or derivatives thereof as disclosed herein are administered by most any means, but are preferable delivered to the patient as an injection (e.g. intravenous, subcutaneous, intraarterial), infusion or instillation, and more preferably by oral ingestion.

Pulsed administration of one or more pharmaceutical compositions comprising a HbF-inducing agent can be used for prophylactic treatment, e.g., for example, a subject who will, or has or is currently undergoing general anesthesia. In some embodiments, pulsed administration can be more effective than continuous treatment as pulsed doses results in the use of an overall lower amount of an anesthesia-reversing agent than would be expected from continuous administration of the same composition. Each pulse dose can be reduced and the total amount of drug administered over the course of treatment to the subject can be minimized. Pulsed administration can provide a saving in time, effort and expense and a lower effective dose can lessen the number and severity of complications that can be experienced by a subject. As such, pulsing can be more effective than continuous administration of the same composition.

In some embodiments, the number of pulses in a single therapeutic regimen can be as little as two, but can be from about 5 to 10, 10 to 20, 15 to 30 or more. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590, which are incorporated herein in their entirety by reference.

In some embodiments, a composition comprising an anesthesia-reversing agent as disclosed herein can be co-administered to a subject concurrently with another agent or treatment regimen, e.g., concurrently at the end of surgery with pain medication or during the withdrawal of the anesthesia agent. In some embodiments, a composition comprising an anesthesia-reversing agent can be co-administered with a pharmaceutical composition comprising an comprising one or more addition agents. The pharmaceutical compositions can also be provided by pulsed administration, concurrently with the anesthesia-reversing agent, or in the periods inbetween the pulse-administration of the anesthesia-reversing agent (e.g., intermittently with the anesthesia-reversing agent). For example, a composition comprising an anesthesia-reversing agent can be administered to a subject, followed by a pain relieving agent after an interval of time has passed, and this order of administration the same or similar time interval can be repeated, for example, at least 1, 2, 3, 4, 5, 6, 7, 8, 9, or 10 or more times.

Pharmaceutical Compositions and Preparations

In some embodiments, a pharmaceutical composition comprising an anesthesia-reversing agent as disclosed herein administered according to a method of the invention can be administered intravenously or orally in effective dosages, depending upon the weight, body surface area, and condition of the subject being treated. In some instances, variations occur depending upon the species of the subject being treated and its individual response to said anesthesia agent or anesthesia-reversing agent as disclosed, as well as on the type of an anesthesia-reversing agent chosen and the time period and interval at which such administration of the anesthesia-reversing agent as disclosed herein is carried out with respect of stopping the administration of the general anesthesia.

In some embodiments, the administration of the pharmaceutical composition comprising an anesthesia-reversing agent as disclosed herein according to a method of the invention is carried out in single or multiple doses. For example, the composition can be administered in a wide variety of different dosage forms, i.e., it may be combined with various pharmaceutically acceptable inert carriers in the form of tablets, dragees, capsules, lozenges, troches, hard candies, aqueous suspensions, elixirs, syrups, and the like. Such carriers include solid diluents or fillers, sterile aqueous media and various non-toxic organic solvents, etc. Moreover, oral pharmaceutical compositions can be suitably sweetened and/or flavored.

In certain embodiments, pharmaceutical compositions comprising an anesthesia-reversing agent as disclosed herein are suitable for intravenous or oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient. When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: filters or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

If desired, pharmaceutical compositions of the present invention may also be formulated to provide slow or controlled release of the active ingredient using, by way of example, hydroxypropyl methyl cellulose in varying proportions; or other polymer matrices, liposomes and/or microspheres. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the particular compositions formulated. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of compositions comprising an anesthesia-reversing agent as disclosed herein generally to ensure their efficacy under normal use circumstances. Especially when employed for treatment of humans and animals in vivo, the practitioner should take all sensible precautions to avoid conventionally known contradictions and toxic effects.

The composition, shape, and type of dosage forms of the invention will typically vary depending on their use. This aspect of the invention will be readily apparent to those skilled in the art. See, e.g., Remington's Pharmaceutical Sciences (1990) 18th ed., Mack Publishing, Eastern Pa.

In certain embodiments, the pharmaceutical compositions of the invention is packaged in a unit dosage form. The term "unit dosage form" or "unit dose" refers to a physically discrete unit suitable for dosing a subject e.g., a patient, i.e., each unit containing a predetermined quantity of active agent calculated to produce the desired therapeutic effect either alone or in combination with one or more additional units. For example, such unit dosage forms may be capsules, tablets, pills, and the like. Unit doses can also be prepared to contain any useful amount of an active ingredient (e.g., an anesthesia-reversing agent). For example, a unit dose can be formulated for about a 5 mg/kg dose, or about a 10 mg/kg dose or about less than 5 mg/kg dose, for example, between a 0.1 mg/kg and 5 mg/kg done, and a unit dose can be, for example, but not limited to, about 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 625 mg, 650 mg, 675 mg, 700 mg, 750 mg, 800 mg, 850 mg, 900 mg, 950 mg, 1000 mg, or more than 1000 mg of an anesthesia-reversing agent as disclosed herein per unit dose. Milligrams per dose can refer to either the free acid form of an anesthesia-reversing agent as disclosed herein, or an anesthesia-reversing agent as disclosed herein in a salt or ester form.

Dosing regimens of an anesthesia-reversing agent as disclosed herein can be tailored to an individual patient, based on any number of clinically relevant parameters including, but not limited to toxicity, tolerance, side-effects, effectiveness, etc.

Combination Therapy

In certain embodiments, a pharmaceutical composition comprising an anesthesia-reversing agent as disclosed herein can be administered alone or in combination with other known compositions administered to a subject, e.g., a mammal emerging or awakening subject from general anesthesia-induced unconsciousness. In some embodiments, mammals include cats, dogs, pigs, horses, cows, rats, mice, monkeys, chimpanzees, baboons, and humans. In specific embodiments, the mammal is a human. In some embodiments, the human is a child. In certain embodiments, the human is under the age of 18. In some embodiments, the human is under the age of 10. In some embodiments, the human is under between the age of 2-7. In embodiments, the subject is under the age of 2. In one embodiment, the subject is at risk of developing emergence delirium, or likely to experience delirium from emergence of general-anesthesia unconsciousness.

The language "in combination with" a known composition is intended to include simultaneous administration of the composition of the invention and the known composition, administration of the composition of the invention first, followed by the known composition and administration of the known composition first, followed by the composition comprising an anesthesia-reversing agent as disclosed herein.

In some embodiments, in addition to the use of an anesthesia-reversing agent as disclosed herein to facilitate awakening from general-anesthesia unconsciousness, concurrent administration of other pharmaceutical and/or nutraceutical compounds can occur. For example, persons can be administered opioids or analgesics (for pain management), and/or antibiotics (for treating secondary infections), and anti-inflammatory agents (to prevent inflammation after surgery). In certain instances, concurrent treatment with an anesthesia-reversing agent as disclosed herein and a second agent occurs at the same time, or on different regimen schedules. In some embodiments an anesthesia-reversing agent as disclosed herein is an orally bio-available compound that is active at well tolerated doses.

Administration of the compositions comprising an anesthesia-reversing agent as disclosed herein may be by oral, parenteral, sublingual, rectal, or enteral administration, or pulmonary absorption or topical application. Compositions can be directly or indirectly administered to the patient.

The compositions comprising an anesthesia-reversing agent as disclosed herein can be purchased commercially and prepared as a mixed composition using techniques well-known to those of ordinary skill in the art.

Direct administration of a composition comprising an anesthesia-reversing agent as disclosed herein to a subject can be by oral, parenteral, sublingual, rectal such as suppository or enteral administration, or by pulmonary absorption or topical application. Parenteral administration may be by intravenous (IV) injection, subcutaneous (s.c.) injection, intramuscular (i.m) injection, intra-arterial injection, intrathecal (i.t.) injection, intra-peritoneal (i.p) injection, or direct injection or other administration to the subject.

Alternatively, pharmaceutical compositions comprising an anesthesia-reversing agent as disclosed herein and/or salts thereof can contain pharmaceutically-acceptable carriers and other ingredients known to facilitate administration and/or enhance uptake (e.g., saline, dimethyl sulfoxide, lipid, polymer, affinity-based cell specific-targeting systems). In some embodiments, a composition comprising an anesthesia-reversing agent as disclosed herein and/or salts thereof can be incorporated in a gel, sponge, or other permeable matrix (e.g., formed as pellets or a disk) and placed in proximity to the endothelium for sustained, local release. In some embodiments, a composition comprising an anesthesia-reversing agent as disclosed herein and/or salts thereof can be administered in a single dose or in multiple doses (e.g., pulses as discussed infra) which are administered at different times.

Pharmaceutical compositions comprising an anesthesia-reversing agent as disclosed herein and/or salts thereof can be administered by any known route. By way of example, a composition comprising an anesthesia-reversing agent as disclosed herein and/or salts thereof can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration of a composition comprising an anesthesia-reversing agent as disclosed herein and/or salts thereof can be made with the goals of achieving a favorable response (e.g., quick awakening without delirium) in the subject who is to emerge from general anesthesia-induced unconsciousness, and avoiding undue toxicity or other harm thereto (i.e., safety). Therefore, "effective" refers to such choices that involve routine manipulation of conditions to achieve a desired effect.

A bolus of the formulation of a composition comprising an anesthesia-reversing agent as disclosed herein and/or salts thereof administered to an individual over a short time after (e.g., immediately after), or immediately before the cessation or stopping of the administration of the anesthesia agent at an appropriate dosing schedule. Alternatively, the effective dose of an anesthesia-reversing agent as disclosed herein can be divided into multiple doses for purposes of administration, for example, two to twelve doses, or more than 12-doses during the awakening period of the subject from the general anesthesia-induced unconsciousness. Dosage levels of active ingredients in a pharmaceutical composition comprising an anesthesia-reversing agent as disclosed herein and/or salts thereof can also be varied so as to achieve a transient or sustained concentration of the compound or derivative thereof in an individual, especially in and around the blood circulation and to result in the desired therapeutic response or protection. But it is also within the skill of the art to start doses at levels lower than required to achieve the desired therapeutic effect and to gradually increase the dosage until the desired effect is achieved.

In some embodiments, the amount of a composition comprising an anesthesia-reversing agent as disclosed herein and/or salts thereof can be administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

Production of compounds comprising an anesthesia-reversing agent as disclosed herein and/or salts thereof according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results aimed at reducing delirium and/or decreasing time to consciousness and functional can vary. Thus, minimum and maximum effective dosages vary depending on the method of administration. Gain of consciousness after anesthesia in a subject can occur within a specific dosage range, which varies depending on, for example, the race, sex, gender, age, and overall health of the subject receiving the dosage of an anesthesia-reversing agent as disclosed herein, the route of administration, whether a composition comprising an anesthesia-reversing agent and/or salts thereof is administered in conjunction with other molecules, or towards the end of the administration of the anesthesia agent or after the stopping of the anesthesia agent, and the specific regimen of administration of the composition comprising an anesthesia-reversing agent and/or salts thereof. For example, in general, intravenous or nasal administration requires a smaller dosage than oral or enteral administration.

Other Formulations and Routes of Administration

In alternative embodiments, a composition comprising an anesthesia-reversing agent as disclosed herein is by an infusion pump (to infuse, for example, the compositions as disclosed herein into the subject's circulatory system) is generally used intravenously, although subcutaneous, arterial, and epidural infusions are occasionally used. Injectable forms of administration of an anesthesia-reversing agent as disclosed herein are sometimes preferred for maximal effect.

Alternatively, in some embodiments, compositions as disclosed herein comprising an anesthesia-reversing agent as disclosed herein and/or salts thereof can also be administered to the nasal passages as a spray, as the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. For example, administration of the compositions as disclosed herein comprising an anesthesia-reversing agent and/or salts thereof to a subject can be oral.

As indicated above, orally active compositions comprising an anesthesia-reversing agent as disclosed herein and/or salts thereof are preferred for at least a portion of the cycle of therapy, as oral administration is usually the safest, most convenient, and economical mode of drug delivery. Consequently, compositions as disclosed herein comprising an anesthesia-reversing agent as disclosed herein can be modified to increase their oral bioavailability by reducing or eliminating their polarity. This can often be accomplished by formulating a composition with a complimentary reagent that neutralizes its polarity, or by modifying the compound with a neutralizing chemical group. Oral bioavailability is also a problem, because drugs are exposed to the extremes of gastric pH and gastric enzymes. Accordingly, problems associated with oral bioavailability can be overcome by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

Compositions as disclosed herein comprising an anesthesia-reversing agent as disclosed herein and/or salts thereof can be physiologically stable at therapeutically effective concentrations. Physiological stable compounds of an anesthesia-reversing agent as disclosed herein or salts thereof not break down or otherwise become ineffective upon administration to a subject or prior to having a desired effect. An anesthesia-reversing agent as disclosed herein can be structurally resistant to catabolism, and, thus, physiologically stable, or coupled by electrostatic or covalent bonds to specific reagents to increase physiological stability. Such reagents include amino acids such as arginine, glycine, alanine, asparagine, glutamine, histidine, or lysine, nucleic acids including nucleosides or nucleotides, or substituents such as carbohydrates, saccharides and polysaccharides, lipids, fatty acids, proteins, or protein fragments. Useful coupling partners include, for example, glycol, such as polyethylene glycol, glucose, glycerol, glycerin, and other related substances.

In some embodiments, compositions as disclosed herein comprising an anesthesia-reversing agent as disclosed herein and/or salts thereof are used in combination with other agents. For example, where the compositions as disclosed herein comprising an anesthesia-reversing agent as disclosed herein and/or salts thereof are being used according to the methods as disclosed herein to reverse general anesthesia-induced unconsciousness and aid recovery of mobility and cognitive function, a combination therapy can include administering a composition comprising an anesthesia-reversing agent as disclosed herein and/or salts thereof and an additional agent, e.g., a pain medication, which are well known in the art, and include for example, but are not limited to opioid analgesics (e.g., morphine and the like) and/or regional anesthesia (i.e. epidurals, nerve blocks, etc). In some embodiments, a pain medication administered with an anesthesia-reversing agent as disclosed herein can include, for example, caffeine, for example ANACIN™, EXCEDRIN™ MIDOL™, VANQUISH™, FIORICET™, ESGIC PLUS™, Cafergot Suppositories (other names: CAFERTRINE™, CAFETRATE™, MIGERGOT™, WIGRAINE™), Cafergot Tablets (other names: ERCAF™, ERGO-CAFF™, GOTAMINE™, WIGRAINE™), FIORINAL™ Capsules, FIORINAL™ with Codeine No. 3, NORGESIC FORTE™; NORPHADRINE FORTE™, NORGESIC™; TRIAMINICIN™ with Codeine Tablets and the like.

Physiological stability of a composition comprising an anesthesia-reversing agent as disclosed herein and/or salts thereof can be measured from a number of parameters such as the half-life of the anesthesia-reversing agent or salts thereof, or the half-life of active metabolic products derived from the anesthesia-reversing agent or salts thereof. In some embodiments, compositions comprising an anesthesia-reversing agent as disclosed herein and/or salts thereof can have in vivo half-lives of greater than about fifteen minutes, greater than about one hour, greater than about two hours, and greater than about four hours, eight hours, twelve hours, or longer. An anesthesia-reversing agent as disclosed herein or its salts can be stable using this criteria, however, physiological stability can also be measured by observing the duration of biological effects on the patient. Clinical symptoms that are important from the patient's perspective include an increased rate of awakening from anesthesia-induced unconsciousness as compared to passive awakening or emergence, or absence of, or decreased occurrence or severity of delirium on awakening as compared to passive awakening from general anesthesia-induced unconsciousness. Preferably, a stable composition comprising an anesthesia-reversing agent and/or salts thereof has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions as disclosed herein comprising a an anesthesia-reversing agent and/or salts thereof are also not significantly biotransformed, degraded, or excreted by catabolic processes associated with metabolism. Although there may be some biotransformation, degradation, or excretion, these functions are not significant, if the composition is able to exert its desired effect.

In some embodiments, compositions as disclosed herein comprising an anesthesia-reversing agent and/or salts thereof are also safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures, and other central nervous system difficulties, fever, bleeding or hemorrhaging, serum abnormalities, and respiratory difficulties.

Compositions useful for facilitating awakening or shortening the awakening period to full cognitive function and mobility after general anesthesia-induced unconsciousness preferably do not substantially affect the effectiveness of the surgery, post-surgery recovery period, or long term cognitive function of the subject.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

Administration of the composition comprising an anesthesia-reversing agent and/or salts thereof to a subject according to a method of the invention may be for prophylaxis, e.g., to any subject awakening from general anesthesia-induced unconsciousness, or alternatively, for therapeutic treatment of a subject identified with emergence delirium or from over sedation by the general anesthesia.

In some embodiments, the composition comprising an anesthesia-reversing agent and/or salts thereof can be used in prophylaxis treatment, for example, where the subject who is at increased risk of delirium, e.g., emergence delirium after general anesthesia, the subject can be administered a composition comprising an anesthesia-reversing agent and/or salts thereof prior to, or concurrent with or subsequent to, the general anesthesia agent, in order to prevent delirium on recovering from unconsciousness.

In some embodiments, the composition comprising an anesthesia-reversing agent and/or salts thereof can be administered to an adult, an adolescent, a child, a neonate, an infant or in utero.

In some embodiments, the composition comprising an anesthesia-reversing agent and/or salts thereof can be administered according to a specific dosing regimen, e.g., in a single or multiple doses, or continuous or sporadic, or as deemed necessary based on an administration regime as determined by recovery of consciousness in the subject as disclosed herein in the Examples.

In some embodiments, a composition comprising an anesthesia-reversing agent and/or salts thereof can be administered to a subject via a continuous infusion throughout the period the subject is recovering consciousness. Alternatively, a composition comprising an anesthesia-reversing agent and/or salts thereof can be administered to the subject in multiple doses over a single span of a few minutes to several hours throughout the period the subject is recovering consciousness.

Alternatively, in some embodiments a composition comprising an anesthesia-reversing agent and/or salts thereof can be administered to a subject in a single parenteral bolus immediately after, or just before stopping the administration of the general anesthesia agent.

In some embodiments, a composition comprising an anesthesia-reversing agent and/or salts thereof can be prepared in solution as a dispersion, mixture, liquid, spray, capsule, or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil, or a relatively inert solid or liquid. Liquids, pills, capsules or tablets administered orally may also include flavoring agents to increase palatability. Additionally, in some embodiments, a composition comprising an anesthesia-reversing agent and/or salts thereof can further comprise agents to increase shelf-life, such as preservatives, anti-oxidants, and other components necessary and suitable for manufacture and distribution of the composition. Compositions comprising an anesthesia-reversing agent and/or salts thereof can further comprise a pharmaceutically acceptable carrier or excipient. Carriers are chemical or multi-chemical compounds that do not significantly alter or affect the active ingredients of the compositions. Examples include water, alcohols such as glycerol and polyethylene glycol, glycerin, oils, salts such as sodium, potassium, magnesium, and ammonium, fatty acids, saccharides, or polysaccharides. Carriers may be single substances or chemical or physical combinations of these substances.

In some embodiments, a composition comprising an anesthesia-reversing agent and/or salts thereof can contain chemicals that are substantially non-toxic. Substantially non-toxic means that the composition, although possibly possessing some degree of toxicity, is not harmful to the long-term health of the patient. Although the active component of the composition may not be toxic at the required levels, there may also be problems associated with administering the necessary volume or amount of the final form of the composition to the patient. For example, if composition comprising an anesthesia-reversing agent contains a salt, although the active ingredient may be at a concentration that is safe and effective, there can be a harmful build-up of sodium, potassium, or another ion. With a reduced requirement for the composition or at least the active component of that composition, the likelihood of such problems can be reduced or even eliminated. Consequently, although patients may suffer minor or short term detrimental side-effects, the advantages of taking the composition outweigh the negative consequences.

In some embodiments, treatment of a subject with a composition comprising an anesthesia-reversing agent and/or salts thereof can be according to the methods as disclosed herein can be therapeutic treatment, e.g., a method of treatment of a emergence delirium or for recovering a subject who is oversedated during general anesthesia. In some embodiments, therapeutic treatment involves administration of a composition comprising an anesthesia-reversing agent and/or salts thereof according to the methods as disclosed herein to a patient suffering from one or more symptoms of, or having been diagnosed as being afflicted with delirium postoperatively, or who is over-sedated by anesthesia during surgery. Therapeutic administration that provides relief and even partial relief from one or more of a symptom of delirium may correspond to an increased quality of surgical experience, and of increased quality of life if the over-sedation is life-threatening. Further, therapeutic treatment or preventative of a subject that alleviate or prevent the occurrence a pathological symptom of delirium can allow for other treatments to be administered, e.g., post-operative wound dressing, pain medication as well as monitoring appropriate post-operative responses.

In alternative embodiments, the treatment of a subject with a composition comprising an anesthesia-reversing agent and/or salts thereof can be according to the methods as disclosed herein can be a prophylactic treatment, for example, to decrease the time to full cognitive function and consciousness after general anesthesia, and/or to prevent the occurrence of delirium in a subject post general-anesthesia unconsciousness. In some embodiments, prophylactic treatments involve administration of a composition comprising an anesthesia-reversing agent and/or salts thereof according to a method of the invention to a subject undergoing general anesthesia, where it is desirable to have the subject emerge from unconsciousness quicker than in the absence of administration of the anesthesia-reversing agent. Administration of a composition comprising an anesthesia-reversing agent and/or salts thereof can begin at the end or immediately after, or during (e.g., concurrent with the decreasing dose of anesthesia agent) administration of an anesthetic agent etc., and can continue, if necessary for a short period of time, after the subject is conscious and gained mobility and cognitive function. As demonstrated herein, both prophylactic and therapeutic uses are readily acceptable, because these compounds are generally safe and non-toxic.

Doses of Administration

The amount of an anesthesia-reversing agent that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

The data obtained from the animal model experiments as disclosed herein in the Examples can be used in formulating a range of dosage for use in humans. The dosage of such compounds lies preferably within a range of circulating concentrations that include the ED50 (the dose therapeutically effective in 50% of the population) with little or no toxicity. The dosage may vary within this range depending upon the dosage form employed and the route of administration utilized.

The therapeutically effective dose of an anesthesia-reversing agent can be estimated initially from animal studies, for example, one can measure the % recovery from consciousness in rats, the rate of recovery to consciousness, respiratory rate and tidal volume, and righting within 30 minutes of administration of an anesthesia-reversing agent, as disclosed herein in the Examples. A dose may be formulated in animal models to achieve a circulating plasma concentration range that includes the $IC_{50}$ (i.e., the concentration of the therapeutic which achieves a half-maximal inhibition of symptoms) as determined in animal models. Levels of an anesthesia-reversing agent in the plasma of an animal model may be measured, for example, by high performance liquid chromatography. The effects of any particular dosage can be monitored by a suitable bioassay.

The dosage of an anesthesia-reversing agent may be determined by a physician and adjusted, as necessary, to suit observed effects of the treatment. Generally, the compositions are administered so that an anesthesia-reversing agent or a prodrug thereof is given at a dose from any of: 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 50 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 0.1 mg/kg to 10 mg/kg includes about 0.1 mg/kg to 1 mg/kg, 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like. In some embodiments, the dose is 0.1 mg/kg to 5 mg/kg, or between about 5 mg/kg to 10 mg/kg.

In some embodiments, the compositions comprising an anesthesia-reversing agent are administered at a dosage so that an anesthesia-reversing agent or a metabolite thereof has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time after the time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once every 10 to 30 minutes depending on a number of clinical factors, such as the subject's sensitivity to an anesthesia-reversing agent. The desired dose can be administered at one time or divided into subdoses, e.g., 2-4 subdoses and administered over a period of time, e.g., at appropriate intervals through the subject awakening to consciousness or other appropriate schedule. Such sub-doses can be administered as unit dosage forms.

An anesthesia-reversing agent or a prodrug thereof can be administrated to a subject in combination with one or more pharmaceutically active agents. Exemplary pharmaceutically active compound include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete content of all of which are herein incorporated in its entirety.

Articles of Manufacture

The invention includes articles of manufacture, which comprise an anesthesia-reversing agent as disclosed herein, e.g., any one or a combination of methylphenidate (MPH), amphetamine, modafinil, amantadine, caffeine, or a prodrug or analogue thereof and labeling stating that the anesthesia-reversing agent is effective for reversing general anesthesia-induced unconsciousness and aiding recovery of cognitive function after general anesthesia. The anesthesia-reversing agent present in this article of manufacture may be methylphenidate (MPH), amphetamine, modafinil, amantadine, caffeine, or a prodrug or analogue thereof. The article of manufacture can comprise the methylphenidate (MPH), amphetamine, modafinil, amantadine, caffeine, or a prodrug or analogue thereof as the only active agent or may include one or more additional active agents or therapeutic agents, e.g., analgesics or pain-reducing agents. Additional active agents may be combined in a single dosage form with the anesthesia-reducing agent, e.g., methylphenidate (MPH), amphetamine, modafinil, amantadine, caffeine, or a prodrug or analogue thereof or may be packaged as separate dosage forms. The article of manufacture may comprise packaging material and a dosage form of anesthesia-reducing agent, e.g., methylphenidate (MPH), amphetamine, modafinil, amantadine, caffeine contained within the packaging material, wherein the packaging material comprises a label approved by a regulatory agency for the product. In certain embodiments the labeling is labeling approved by the United States FDA.

An example of an article of manufacture provided by the invention is a packaged pharmaceutical compositions comprising an anesthesia-reducing agent, e.g., any one or a combination of methylphenidate (MPH), amphetamine, modafinil, amantadine, caffeine in a container and printed labeling stating that the anesthesia-reducing agent, e.g., methylphenidate (MPH), amphetamine, modafinil, amantadine, caffeine is useful for reversing general anesthesia-induced unconsciousness and aiding recovery of cognitive function after general anesthesia.

When an article of manufacture of this invention comprises methylphenidate (MPH), the labeling may advise administering a range between 10 mg/kg to 5 mg/kg, or 5 mg/kg to 0.1 mg/kg per dose to awaken a subject from anesthesia-induced unconsciousness. The labeling can also advise that methylphenidate (MPH) is to be administered via intravenous administration, but there can be alternative routes by which methylphenidate (MPH) can be administered.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference

EXAMPLES

Materials and Methods.

Animal Care and Use. Animal studies were approved by the Subcommittee on Research Animal Care, Massachusetts General Hospital, Boston, Mass. Male Sprague-Dawley rats (Charles River Laboratories, Wilmington, Mass.) weighing 351-565 grams were used. For the experiments to determine time to emergence, as well as the methylphenidate dose-response studies under continuous isoflurane general anesthesia, experiments were performed using the same 12 rats in random order. Separate groups of animals were used for the electroencephalogram (4 rats), plethysmography (4 rats), and blood gas studies (6 rats). In animals that underwent multiple experiments, each animal was provided with at least 3 days of rest between experiments. Animals were kept on a standard day-night cycle (lights on at 7 AM, and off at 7 PM), and all experiments were performed during the day.

Anesthetizing Protocol. Rats were anesthetized in an induction chamber with 2-3% isoflurane in oxygen prior to placement of a lateral tail vein intravenous catheter (24 gauge, 19 mm). A rectal temperature probe was inserted and the animal was placed in a cylindrical acrylic anesthetizing chamber. The chamber was custom-built and equipped with ports for anesthetic gas delivery, sampling, and scavenging, as well as intravenous drug administration. A heating pad was placed under the chamber to keep the animal warm, and the body temperature was kept between 36.5° C. and 37.4° C.

The volume of the chamber was 4.6 liters. Initially the chamber was primed with isoflurane at a fresh gas flow rate of 2-3 liters/min, and then the rate was lowered to 1-2 liters/min. The carrier gas was oxygen. Gas was continuously sampled from the distal portion of the chamber (opposite from the fresh gas inlet) and isoflurane, oxygen, and carbon dioxide concentrations in the chamber were monitored using a calibrated Ohmeda 5250 anesthetic agent analyzer (GE Healthcare, Waukesha, Wis.).

Preparation and Delivery of Drugs. Isoflurane, methylphenidate hydrochloride, and droperidol were purchased from Henry Schein (Melville, N.Y.), Sigma-Aldrich (St. Louis, Mo.), and American Regent (Shirley, N.Y.), respectively. Normal saline, methylphenidate, and droperidol were always administered intravenously. Methylphenidate was weighed, dissolved in 0.5 ml of normal saline, and sterile filtered immediately prior to administration. Droperidol was diluted in normal saline to a final volume of 0.5 ml prior to administration. The intravenous tubing (approximate volume 0.6 ml) was always flushed with 2 ml of normal saline after methylphenidate or droperidol to ensure complete delivery of drug.

Time to Emergence after a Standardized Isoflurane General Anesthetic. To test the hypothesis that methylphenidate decreases time to emergence from a standardized isoflurane anesthetic, an endpoint that has been used in several recent studies of anesthetic emergence,[5,6,10] the inhaled concentration of isoflurane was fixed at 1.5% (~1 MAC). After 40 minutes, rats received either normal saline or methylphenidate (5 mg/kg IV). Isoflurane was continued for five additional minutes, then the rat was taken out of the chamber and the temperature probe was removed. The animal was placed supine on a warming pad and inspired room air. Time to emergence was defined as the time from termination of isoflurane to return of righting (i.e. all four paws touching the floor).

Administration of Methylphenidate During Continuous Isoflurane General Anesthesia. The rat was positioned supine in the anesthetizing chamber and the inhaled concentration of isoflurane was initially fixed at 2.0% for 20 minutes, then reduced to 0.8% over 15-20 minutes, and then maintained at 0.8% for 40 minutes. If the rat made any purposeful movement, the isoflurane concentration was increased by 0.1% and maintained for another 40 minutes. This process was repeated until the final dose of isoflurane sufficient to maintain loss of righting reflex was established, and this dose was administered throughout the remainder of the experiment. This protocol was based on previously published methods described by Alkire et al.[4,11] After the final 40-minute equilibration period, normal saline (2 ml) was administered and the rectal temperature probe was removed. Five minutes later, methylphenidate was administered. To establish a dose-response relationship, the inventors administered three different doses of methylphenidate (0.05 mg/kg, 0.5 mg/kg, or 5 mg/kg IV) on different days. After administration of methylphenidate, each animal continued to inhale the same dose of isoflurane for 30 minutes, or until restoration of righting occurred.

Electroencephalogram electrode placement, recording, and spectral analysis. Extradural electroencephalogram electrodes were surgically implanted at least 7 days prior to recording. General anesthesia was induced with xylazine (5-10 mg/kg IP) and ketamine (50-100 mg/kg IP), and supplemented with isoflurane (1-2%). A microdrill was used to make four holes at the following stereotactic coordinates: A0L0, A6L3, A6L-3, and A10L2 relative to the lambda.[12] Polytetrafluoroethylene coated, 200 μm diameter stainless steel electrode wires (A-M Systems, Sequim, Wash.) were inserted and secured with small stainless steel screws, and permanently fixed with dental acrylic cement. Carprofen (5 mg/kg SC) was administered for analgesia on the day of surgery, as well as on post-operative days 1, and 2. The potential difference between electrodes A0L0 and A6L3, or between electrodes A0L0 and A6L-3 (whichever gave less motion artifact), was referenced to A10L2 and recorded using a QP511 Quad AC Amplifier System (Grass Instruments, West Warwick, R.I.) and a USB-6009 14-bit data acquisition board (National Instruments, Austin, Tex.). Data was filtered between 0.3-100 Hz. No line filter was used. The sampling rate was 512 Hz. After baseline recordings were taken for 10 minutes while awake, rats were anesthetized with isoflurane and placed in the anesthetizing chamber. Although the inventors initially attempted to perform the electroencephalogram experiments simultaneously with the behavioral experiments described above, the inventors found that the righting attempts produced too many motion artifacts. Therefore the inventors performed the electroencephalogram experiments in the prone position with the isoflurane dose fixed at 1.0%. These modifications allowed us to minimize electroencephalogram motion artifacts without restraining the animals. After a minimum isoflurane exposure of 40 minutes, normal saline was administered and the temperature probe was removed. Five minutes later, methylphenidate was administered. Spectral analysis was performed using Matlab 7.11 (Mathworks, Natick, Mass.) and the Chronux software (Cold Spring Harbor, N.Y.).[13] Spectrograms were calculated using sliding windows of 2 sec duration stepped through 0.05 sec. For each window, multitaper spectrum estimation was performed using 5 tapers. The resulting spectral estimates have a bandwidth of ±1.5 Hz. Mean power spectra were compared before and after methylphenidate administration using Kolmogorov-Smirnov tests.14 To determine the difference between two spectra, a two sample Kolmogorov-Smirnov test 15 was performed on the spectral power as a function of frequency computed from the 30 windows in the pre-methylphenidate and post-methylphenidate periods. The inventors used a Bonferroni correction to adjust the significance level for multiple hypothesis testing.

Plethysmography. Rats were placed in a custom built plethysmography chamber and the isoflurane concentration in the chamber was maintained at 1.5%. After equilibration in the chamber for 30 minutes, normal saline or droperidol (0.5 mg/kg IV) was administered five minutes prior to methylphenidate (5 mg/kg IV). Because plethysmography recordings are very sensitive to motion artifacts, the inventors used a higher isoflurane dose (1.5% or ~1 MAC), since animals at this dose of isoflurane did not exhibit purposeful movements after methylphenidate was administered. A differential pressure transducer and demodulator (Models CD15 and MP45-14-871; Validyne Engineering, Northridge, Calif.) were used to convert the chamber pressure to an analog signal. The signal was high pass filtered at 15 sec, acquired at 100 Hz, and analyzed in four second epochs using a USB-6009 data acquisition board (National Instruments, Austin, Tex.) and LabView Software (version 8.5 for Macintosh). Chamber carbon dioxide levels were maintained at or less than 0.5% in the open flow configuration. A heating pad was used to warm the rat from beneath. Chamber air temperature and relative humidity were measured with a thermometer-hygrometer (Fisher Scientific, Pittsburgh, Pa.) and used to estimate tidal volumes during intermittent chamber closure using methods described by Drorbaugh et al.[16]

Arterial Blood Gas and Hemodynamic Recordings. Rats with femoral artery catheters (Charles River Laboratories, Wilmington, Mass.) were placed in the anesthetizing chamber after lateral tail vein IV catheter placement. The isoflurane dose was kept constant at 1.5%. Mean arterial blood pressure and heart rate were measured using a pressure transducer (TruWave, Edwards Life Sciences, Irvine, Calif.) interfaced with a custom-built amplifier (AD620 operational amplifier, Jameco Electronics, Belmont, Calif.). The signal was digitized at 1,000 Hz using a USB-6009 data acquisition board (National Instruments, Austin, Tex.) and analyzed in four-second epochs. A pre-methylphenidate arterial blood sample was drawn following at least 30 minutes of equilibration in 1.5% isoflurane, and a postmethylphenidate sample was drawn 15 minutes after methylphenidate administration. Samples were promptly analyzed using CG4+ cartridges in a Vetscan iStat 1 (Abaxis, Union City, Calif.) blood gas analyzer.

Statistical analysis of the effect of methylphenidate on emergence times, return of righting responses and spectrograms. Prism 4.03 (Graphpad Software, San Diego, Calif.) and Matlab (Mathworks, Natick, Mass.) were used for statistical analysis and where possible, results are reported in terms of 95% confidence intervals based on z-tests, t-tests or Mann-Whitney tests. The inventors used a Bayesian Monte Carlo procedure to compute Bayesian 95% (credibility) confidence intervals to assess the effect of methylphenidate dose on return of righting during continuous isoflurane general anesthesia[17]. For this computation the inventors assumed a binomial model as the sampling density or likelihood function for the propensity of animals in a given group to have return of the righting response. The inventors took as the prior density for each group the uniform density on the interval (0, 1) because it is uninformative. Because of the conjugacy between the prior and the likelihood the posterior density for each group is a beta density.[17] The posterior densities for the differences in the proportion of animals that had return of righting were then computed by using standard Matlab simulation procedures. Instead of p-values for the Bayesian analyses the inventors computed the posterior probability that the propensity to right was greater in on group compared to the other.

A one-way ANOVA was used to assess whether there were significant differences among the final isoflurane doses of animals that received the 3 different doses of methylphenidate. To provide a conservative check on the assessments made by the 95% confidence intervals and the parametric tests and non-parametric tests were also used to assess statistical significance. The Mann-Whitney test was used to test the hypothesis that methylphenidate hastens time to emergence from isoflurane general anesthesia, and to test the dose-dependence of methylphenidate on time to righting during continuous isoflurane general anesthesia. A paired t-test was used to test the hypothesis that methylphenidate produces a respiratory alkalosis during isoflurane general anesthesia. The inventors used the two-sided Kolmogorov-Smirnov test with a Bonferonni correction to compare spectra in animals before and after receiving methylphenidate. The inventors considered a result to be statistically significant based on the 95% confidence intervals comparing two groups if zero was not in the interval, based on hypothesis tests if the p-values were less than 0.05 or in the case of the Bayesian analyses, if the relevant posterior probability was greater than 0.95.

Statistical analysis of the effect of methylphenidate on respiratory rate, mean arterial blood pressure, and heart rate. To estimate the effect of methylphenidate on respiratory and cardiovascular variables, the inventors performed within-animal analyses because the inventors had sufficient samples to estimate the mean of each variable and its standard error before and after drug administration for each animal. To do so, the inventors performed time-series modeling of these measurements to take account of their serial dependence and thereby, compute appropriate estimates of variance for within-animal two sample z-tests. That is, the inventors fit different autoregressive models of order p (AR(p)) with a nonzero mean to the data before and after the administration of methylphenidate. Because these models have a non-zero mean, the inventors devised an efficient cyclic descent parameter estimation algorithm.[18] Within the cyclic descent algorithm the inventors used the least-squares algorithm to estimate the AR parameters and conditional maximum likelihood estimation to compute the mean and variance parameters.[14] The cyclic descent algorithm iterated between the least-squares and the conditional maximum likelihood procedures until convergence was achieved. The inventors allowed the order of the AR (p) model to be different for each segment. The inventors chose the best order p of the AR model on each segment using Akaike's Information Criterion.[14] The inventors computed the approximate standard errors of the parameters by estimating the parameter covariance matrix as the inverse of the observed Fisher information matrix.[19] By design, these standard errors of the parameters take account of the serial dependence in the data. The estimated mean and standard error of the mean were used to compute the 95% confidence interval for the difference between the physiological variable before and after methylphenidate based on a z-statistic.

Example 1

The inventors herein assessed if methylphenidate (MPH) induces emergence from isoflurane anesthesia. The inventors first tested whether methylphenidate affects time to emergence from a standardized general anesthetic with isoflurane. The inventors then assessed two possible mechanisms by which methylphenidate may act: (1) increased arousal, or (2) increased minute ventilation. To test for increased arousal, the inventors performed experiments to assess whether methylphenidate induces restoration of righting under continuous isoflurane anesthesia. The inventors also performed spectral analysis of electroencephalogram recordings to assess changes induced by methylphenidate during continuous isoflurane anesthesia. To test for increased minute ventilation, the inventors obtained plethysmography and arterial blood gas data to analyze changes in respiratory status induced by methylphenidate.

Thus, one aspect of the present invention is based on the inventors discovery that in a rat animal model, intravenous dextro-methylphenidate (d-MPH), levo-MPH, and racemic MPH rapidly reversed isoflurane-induced general anesthesia. The inventors next assessed if other drugs may be clinically useful to actively reverse general anesthesia. One aspect of the present invention is directed to use of dextro-amphetamine, amphetamine, modafinil, amantadine, caffeine, or a product containing any of these drugs, to reverse the state of general anesthesia when it is no longer desired (e.g. at the end of surgery).

Accordingly, herein the inventors demonstrate that anesthesia-reversing agents dextro-amphetamine, amphetamine, modafinil, amantadine, caffeine, or a product containing any of these drugs, prepared as a sterile solution for intravenous injection can be used for reversing effects of general anesthesia. The inventors compositions comprising anesthesia-reversing agents have a widespread usefulness in patients to rapidly reverse the state of general anesthesia when it is no longer desired (e.g. at the end of surgery). In addition, anesthesia-reversing agents are useful as a "rescue" drug in patients who are accidentally oversedated and become unresponsive or apneic during conscious sedation. Finally, the anesthesia-reversing agents as disclosed herein also have utility for the treatment of emergence delirium, a serious clinical problem with an incidence as high as 30% in pediatric patients undergoing general anesthesia.

Using adult rats, the inventors assessed the effect of methylphenidate IV on time to emergence from isoflurane anesthesia. The inventors then performed experiments to test separately for methylphenidate-induced changes in arousal and changes in minute ventilation. A dose response study was performed to test for methylphenidate-induced restoration of righting during continuous isoflurane anesthesia. Surface electroencephalogram recordings were performed to observe neurophysiological changes. Plethysmography recordings and arterial blood gas analysis were performed to assess methylphenidate-induced changes in respiratory function. Droperidol IV was administered to test for inhibition of methylphenidate's actions.

Example 2

Figure 1B:
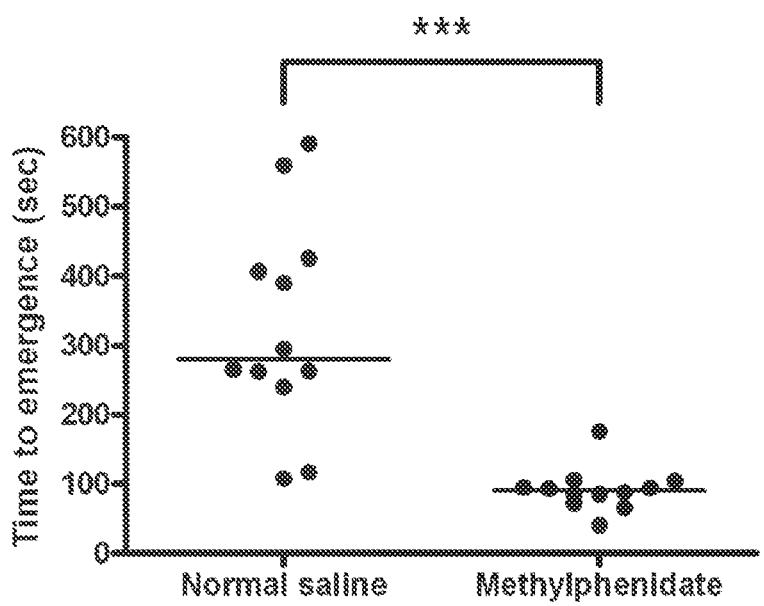
Figure 7:
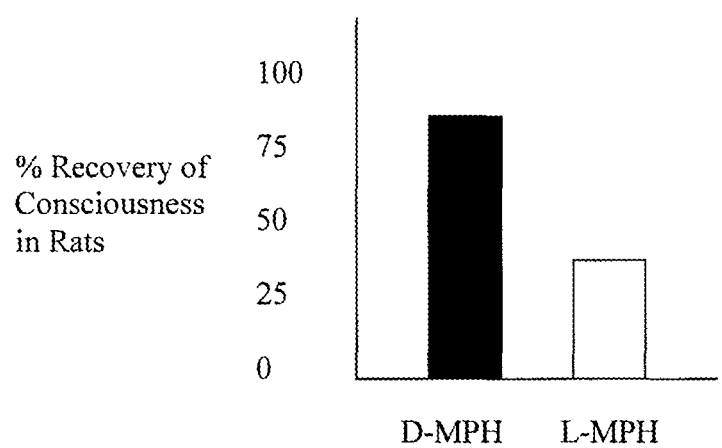
FIG. 7 show dexo-methylphenidate (D-MPH) decreases time to emergence from isoflurane anesthesia at a quicker rate than L-MPH.

Methylphenidate hastens time to emergence from a standardized isoflurane anesthetic. FIG. 1A provides a schematic of the protocol for this experiment. As shown in FIG. 1B, the median time to emergence for animals that received normal saline was 280 seconds (n=12), versus 91 seconds (n=12) for animals that received methylphenidate (5 mg/kg IV). The median difference in time to emergence between these two groups was 200 seconds with a 95% confidence interval computed using the Mann-Whitney test of [155, 331] seconds. This median difference was statistically significant (p<0.0001, two-sided Mann-Whitney test). The % recovery of consciousness in rats of was faster for D-MGH than L-MPH, as shown in FIG. 7.

Methylphenidate Induces Emergence During Continuous Inhalation of Isoflurane

To assess if methylphenidate increases arousal, the inventors performed the following experiments during continuous inhalation of isoflurane. Because isoflurane was not discontinued, any emergence mechanism involving accelerated isoflurane excretion would not be possible. At the start of these experiments (FIG. 2A) the minimum concentration of inhaled isoflurane sufficient to maintain loss of righting was established for each rat (see Materials and Methods for details), and this dose was continuously delivered to the chamber throughout the experiment. The final dose of isoflurane was 0.9%±0.1% (mean±SD). After equilibration, none of the animals exhibited purposeful movement in response to intravenous injection of normal saline or removal of the temperature probe, indicating that mild stimulation did not produce arousal at this depth of anesthesia. Five minutes after normal saline, methylphenidate was administered. At the maximum dose of 5 mg/kg, purposeful movements (e.g. lifting of the head, opening of the eyes, twisting of the torso, kicking, clawing, chewing, licking, and grooming) were observed within 30 seconds for all 12 rats, despite continuous inhalation of isoflurane at the same, fixed dose. All of the rats remained very active and continued to move about in the chamber after righting. Per the animal protocol, the inventors concluded the experiment after the righting reflex was restored. As shown in FIG. 2B, return of righting occurred in 11 of 12 rats after administration of methylphenidate at this dose. Return of righting also occurred in 11 of 12 rats after administration of a 10-fold lower dose (0.5 mg/kg IV), but there were no signs of arousal in any of the six rats that received 0.05 mg/kg. The Bayesian 95% confidence interval for the difference in the propensities to have return of righting between rats in the 5 mg/kg methylphenidate group and those in the 0.05 mg/kg methylphenidate group was [0.39, 0.94]. The Bayesian 95% confidence interval for the difference in the propensities to have return of righting between rats in the 0.5 mg/kg methylphenidate group and those in the 0.05 mg/kg methylphenidate group was [0.40, 0.94]. For both comparisons the posterior probability was 0.999 indicating that the two differences are highly significant. As shown in FIG. 2C, the median time to righting after methylphenidate during continuous inhalation of isoflurane was 181 seconds for rats that received 5 mg/kg, and 348 seconds for rats that received 0.5 mg/kg. The median difference in time to righting during continuous inhalation of isoflurane between these two groups was 173 seconds with a 95% confidence interval computed using the Mann-Whitney test of [50, 332] seconds. This median difference was statistically significant (p=0.01, two-sided Mann-Whitney test). There was no statistically significant difference in the final isoflurane dose among the animals that received the 3 different doses of methylphenidate (p=0.3, F-test for one-way ANOVA).

Example 3

Droperidol Inhibits Methylphenidate-Induced Emergence Behavior

Figure 2A:
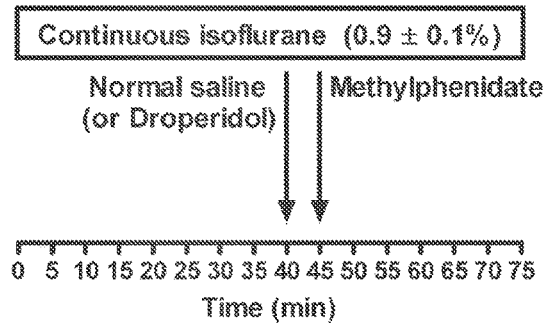
FIGS. 2A-2D show methylphenidate induces emergence during continuous inhalation of isoflurane.
Figure 2B:
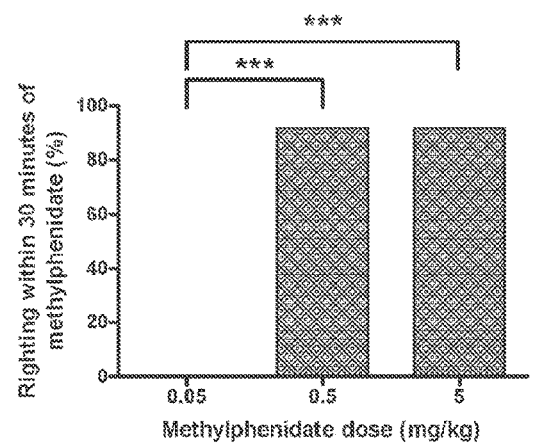
Figure 2C:
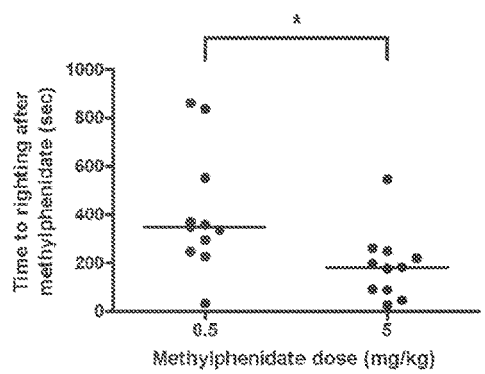
Figure 2D:
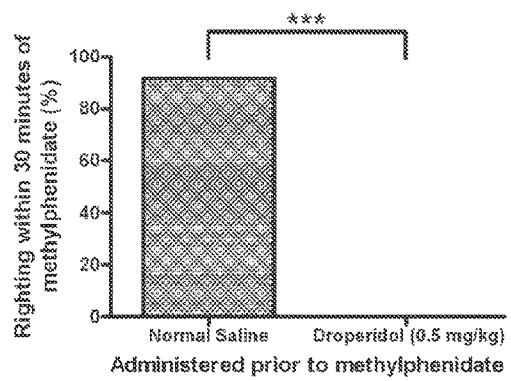

In a group of animals (n=6) continuously inhaling isoflurane at a dose sufficient to maintain loss of righting as above, the protocol illustrated in FIG. 2A was repeated with the exception that droperidol (0.5 mg/kg IV) was administered in place of normal saline. None of the animals exhibited purposeful movement in response to the administration of droperidol or subsequent removal of the temperature probe. Five minutes after droperidol, the highest dose of methylphenidate used in this study (5 mg/kg) was administered. These animals generally exhibited no purposeful movement after methylphenidate administration, although some sluggish limb movements were occasionally observed. None of these animals had return of righting, compared to the 11 of 12 animals that had return of righting after receiving normal saline prior to the same dose of methylphenidate (FIG. 2D). The 95% Bayesian confidence interval for the difference in righting propensity between these two conditions is [0.39, 0.94]. The posterior probability that the propensity to right for those that received saline was greater than that for those that received droperidol was 0.999, indicating a highly significant difference.

Droperidol Inhibits Methylphenidate-Induced Electroencephalogram Changes During Continuous Inhalation of Isoflurane.

Figure 3A:
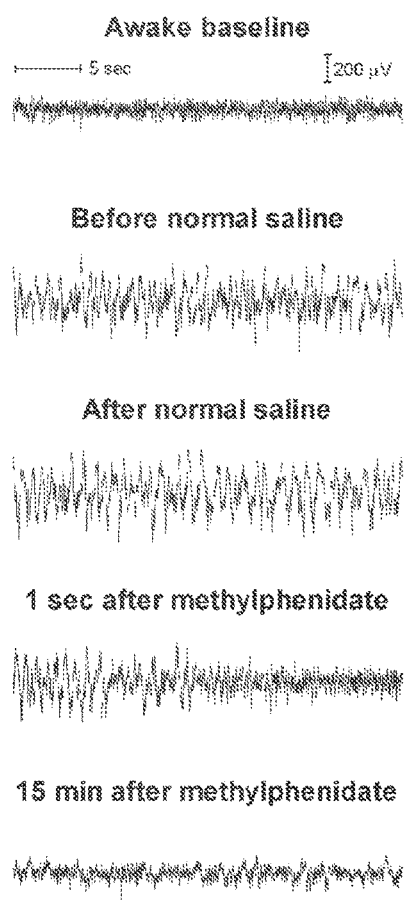
FIGS. 3A-3B shows methylphenidate-induced electroencephalogram changes during continuous inhalation of isoflurane are inhibited by droperidol.
Figure 3B:
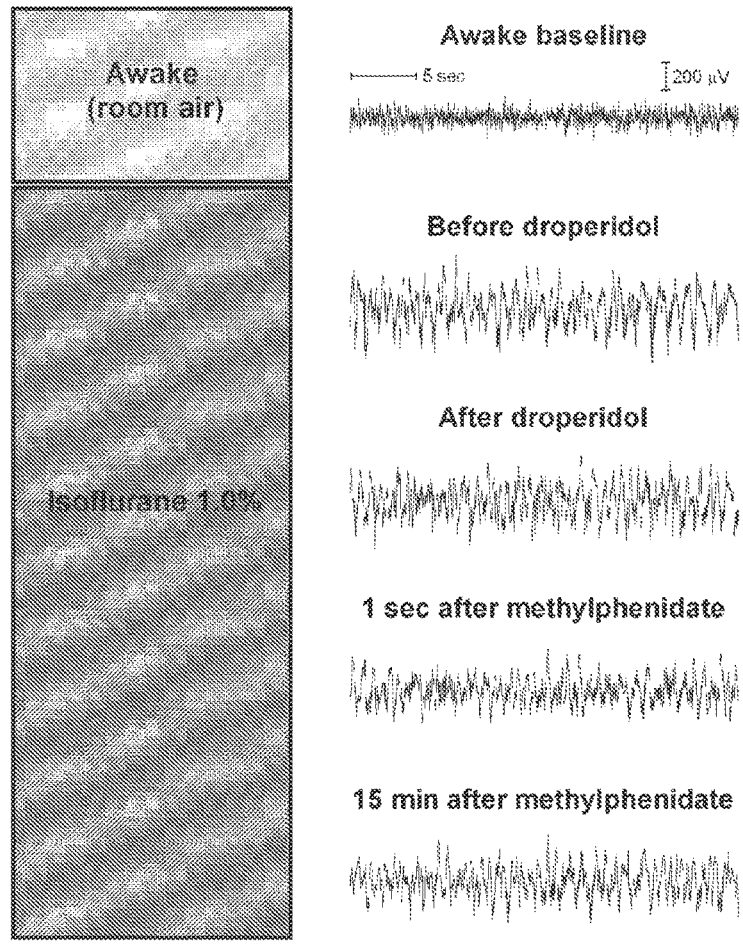

Electroencephalogram data was recorded from rats with pre-implanted extradural skull electrodes (n=4). Results from an individual rat are shown in FIG. 3A. In the awake state before the administration of any drugs, animals showed an active high-frequency, low-amplitude electroencephalogram pattern, which changed to a low-frequency, high-amplitude pattern during continuous inhalation of isoflurane (1.0%). Although the electroencephalogram pattern did not change after injection of normal saline or removal of the temperature probe, administration of methylphenidate (5 mg/kg IV) induced a prompt shift within 30 seconds back to an active high frequency, low-amplitude pattern similar to that observed during the awake state. This change persisted for more than 15 minutes. FIG. 3B shows 30-second epochs of raw electroencephalogram recordings from a single animal that received droperidol (0.5 mg/kg IV) five minutes prior to methylphenidate (5 mg/kg IV). After droperidol administration, methylphenidate did not induce electroencephalogram changes consistent with arousal.

To assess changes in electroencephalogram power over time, spectrograms were computed from the continuous electroencephalogram data recorded from each animal. Typical results from individual rats are shown in FIG. 4. During the awake state (FIG. 4A), electroencephalogram power was mainly in the theta frequency range (4-8 Hz). However, continuous inhalation of 1.0% isoflurane (FIG. 4B) caused a large increase in delta power (<4 Hz). Although intravenous injection of normal saline produced no appreciable change in the power spectrum, administration of methylphenidate (5 mg/kg IV) produced a prompt shift in power from delta to theta. When droperidol (0.5 mg/kg IV) was administered instead of normal saline, however, methylphenidate failed to induce these electroencephalogram changes (FIG. 4C).

Figure 5A:
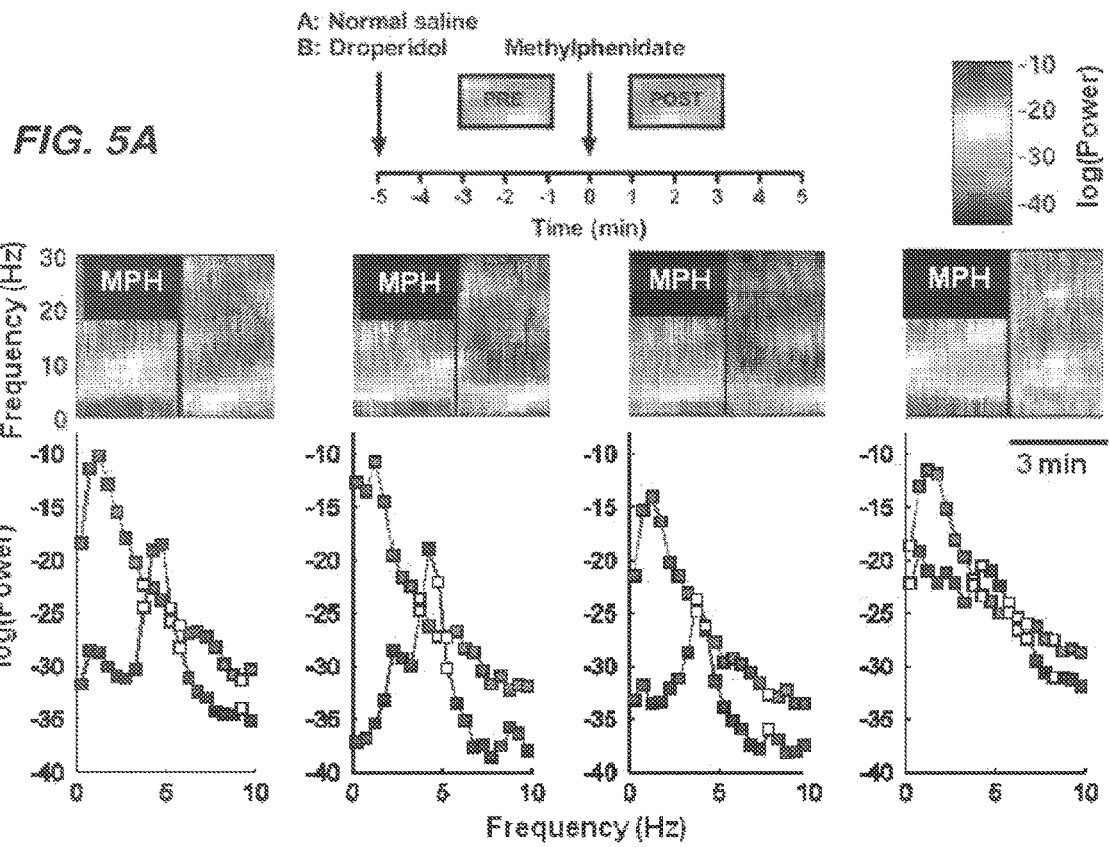
FIGS. 5A-5B show an electroencephalogram power spectra and spectrograms computed for each of 4 animals reveal a shift in peak power from delta to theta after administration of methylphenidate that is inhibited by droperidol. The top panel shows the two-minute windows used to compute power spectra before methylphenidate administration (red, "PRE"), and after methylphenidate administration (blue, "POST").
Figure 5B:
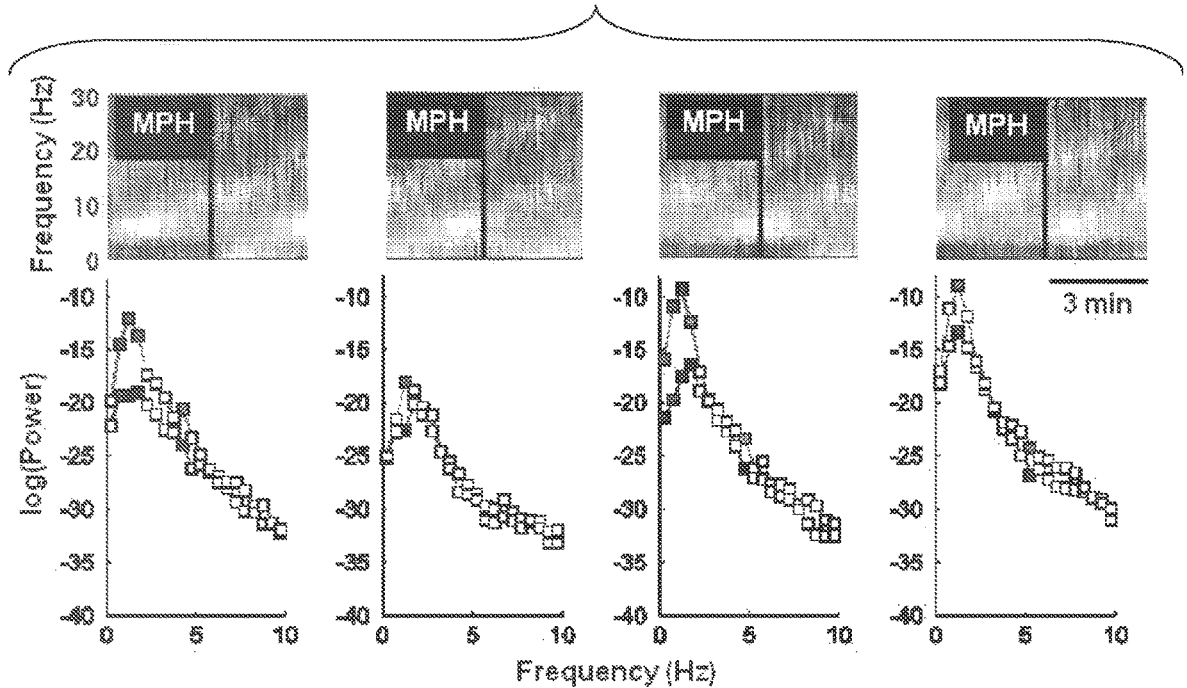

FIG. 5 shows spectrograms and power spectra with the results of the Kolmogorov-Smirnov test computed from two-minute time windows before and after methylphenidate administration. At a 0.05 significance level the two-sided Kolmogorov-Smirnov test with Bonferonni correction rejects the null hypothesis at all frequencies except those marked with white squares. In four rats that received normal saline (FIG. 5A), methylphenidate (5 mg/kg IV) induced a rapid shift in peak power from delta to theta, and the difference in power before and after methylphenidate was statistically significant at most frequencies between 0-10 Hz (twosided Kolmogorov-Smirnov test, p<0.05). However, as shown in FIG. 5B, four rats that received droperidol (0.5 mg/kg IV) prior to methylphenidate only had small, statistically significant decreases in delta power (two-sided Kolmogorov-Smirnov test, p<0.05), and the shift in peak power from delta to theta was absent.

of the four rats had statistically significant changes in tidal volume, the changes were small and inconsistent. As demonstrated in the typical result shown in FIG. 6B, when droperidol (0.5 mg/kg IV) was administered instead of normal saline five minutes prior to methylphenidate (5 mg/kg IV), there was only a negligible increase in respiratory rate. Within-animal analysis revealed that methylphenidate produced a statistically significant increase in respiratory rate in each of these animals that ranged from 2 to 5 breaths per minute (Table 2, two-sided z-test within-animal corrected for serial correlation, all p<0.0001). However, those increases were appreciably smaller than the 10 to 51 breaths per minute increases observed in the animals that were pretreated with normal saline. Although all four rats had statistically significant changes in tidal volume, the changes were small (4-17%) and inconsistent (one had an increase, while the other three had decreases).

TABLE 1

Respiratory rate (RR, breaths per minute) in individual animals pretreated with normal saline during isoflurane general anesthesia. Cl = confidence interval, RR = respiratory rate.

| Animal | 1 | 2 | 3 | 4 |
| --- | --- | --- | --- | --- |
| RR before methylphenidate (mean, [95% Cl]) | 83.4 [81.5, 85.4] | 84.3 [83.5, 85.2] | 103.5 [98.4, 108.5] | 97.8 [96.3, 99.3] |
| RR after 5 mg/kg IV Methylphenidate (mean, [95% Cl]) | 112.6 [109.5, 115.7] | 94.2 [93.4, 95.0] | 153.8 [150.5, 157.2] | 116.7 [114.0, 119.4] |
| Change in mean RR (mean, 95% Cl]) | +29.2 [+25.5, +32.9] | +9.8 [+8.7, +11.0] | +50.36 [+44.3, +56.4] | +18.9 [+15.8, +21.9] |
| z-statistic | 15.9 | 16.6 | 16.7 | 12.3 |
| p-value | $<10^{-16}$ | $<10^{-16}$ | $<10^{-16}$ | $<10^{-15}$ |

TABLE 2

Respiratory Rate (RR, breaths per minute) in individual animals pretreated with droperidol (0.5 mg/kg IV) during isoflurane general anesthesia. Cl = confidence interval, RR = respiratory rate.

| Animal | 1 | 2 | 3 | 4 |
| --- | --- | --- | --- | --- |
| RR before methylphenidate (mean, [95% Cl]) | 81.9 [80.7, 83.0] | 75.8 [75.2, 76.4] | 80.5 [79.8, 81.2] | 70.6 [69.2, 72.0] |
| RR after 5 mg/kg IV Methylphenidate (mean, [95% Cl]) | 86.3 [85.8, 86.8] | 78.0 [77.1, 78.9] | 84.1 [83.4, 84.9] | 75.5 [74.9, 76.1] |
| Change in mean RR (mean, 95% Cl]) | +4.4 [3.2, +5.7] | +2.2 [+1.1, +3.3] | +3.6 [+2.6, +4.6] | +4.9 [+3.3, +6.4] |
| z-statistic | 7.0 | 4.1 | 7.0 | 6.3 |
| p-value | <0.0001 | <0.0001 | <0.0001 | <0.0001 |

Example 4

Methylphenidate Induces an Increase in Minute Ventilation that is Inhibited by Droperidol.

Figure 6A:
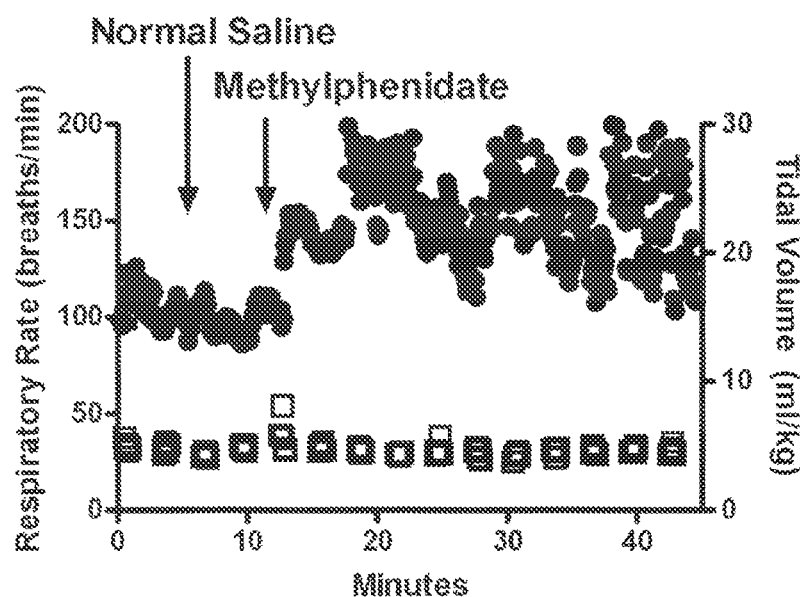
FIGS. 6A-6B show methylphenidate induces an increase in respiratory rate that is inhibited by droperidol.
Figure 6B:
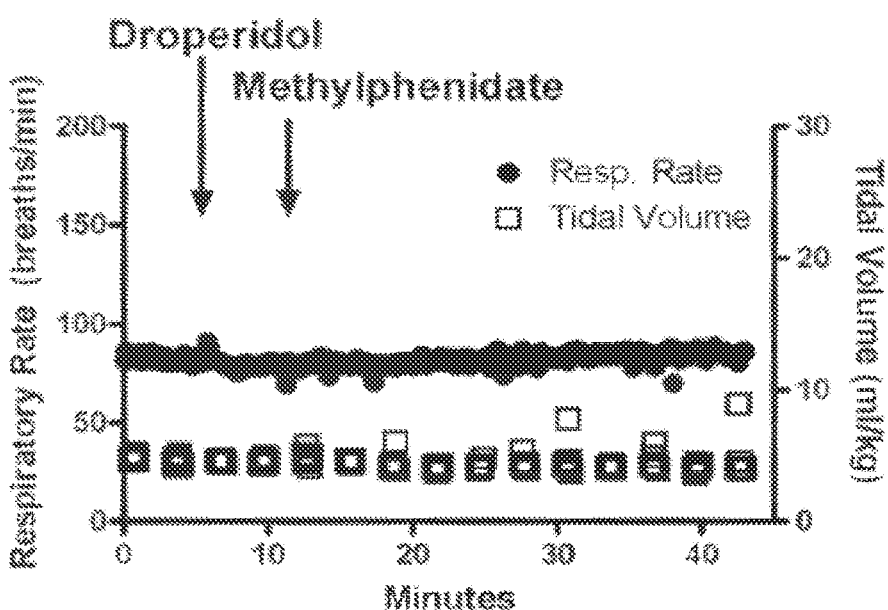

As demonstrated in the representative result shown in FIG. 6A, methylphenidate (5 mg/kg) induced a substantial increase in respiratory rate during continuous inhalation of isoflurane (1.5%). At this dose of isoflurane, purposeful movements consistent with arousal were not induced by methylphenidate. Within-animal analysis demonstrated that methylphenidate induced a statistically significant increase in respiratory rate for each animal that ranged from 10 to 51 breaths per minute (Table 1, two-sided z-test within-animal corrected for serial correlation, all p<10-16). Although two Methylphenidate Induces a Significant Respiratory Alkalosis and Small Hemodynamic Changes During Isoflurane General Anesthesia.

As shown in Table 3, during continuous isoflurane anesthesia there were statistically significant changes in arterial pH and paCO2 after the administration of methylphenidate. Assuming no change in baseline metabolism, the calculated increase in alveolar ventilation (VA) was 24±6% using the relationship VApost/VApre=(paCO2)pre/(paCO2)post, where "pre" and "post" denote pre-methylphenidate and post-methylphenidate, respectively. The slight increase in PaO2 after methylphenidate was not statistically significant (two-sided paired t test, p=0.14). Within-animal analyses showed that 4 animals had statistically significant increases in mean arterial blood pressure (3 to 20 mmHg) while 2 had no significant change (Table 4). Four animals had insignificant increases in heart rate and 2 had small, but statistically significant increases (6 and 15 beats per minute) in heart rate (Table 5).

TABLE 3

Arterial blood gas analysis during isoflurane general anesthesia (n = 6). CI = confidence interval, RR = respiratory rate.

|  | pH | $P_2CO_2$ (mmHg) | $P_2O_2$ (mmHg) |
|---|---|---|---|
| before methylphenidate (mean, [95% CI]) | 7.45 [7.41, 7.50] | 43 [40, 47] | 226 [200, 252] |
| after 5 mg/kg IV Methylphenidate (mean, [95% CI]) | 7.51 [7.46, 7.55] | 35 [32, 38] | 241 [211, 270] |
| p-value (paired t test) | 0.004 | 0.0001 | 0.144 |

TABLE 4

Mean arterial blood pressure (MAP, mmHg) in individual animals during isoflurane general anesthesia. CI = confidence interval, RR = respiratory rate.

|  | Animal | | | | | |
|---|---|---|---|---|---|---|
|  | 1 | 2 | 3 | 4 | 5 | 6 |
| MAP before methylphenidate (mean, [95% CI]) | 96.6 [96.3, 96.9] | 82.6 [81.7, 83.5] | 88.1 [87.7, 88.4] | 86.7 [86.1, 87.2] | 100.2 [99.7, 100.8] | 83.4 [82.7, 84.1] |
| MAP after 5 mg/kg IV Methylphenidate (mean, [95% CI]) | 117.1 [116.1, 118.0] | 90.9 [90.0, 91.7] | 91.3 [91.0, 91.5] | 85.2 [85.0, 85.5] | 100.7 [100.3, 101.2] | 90.8 [89.4, 92.2] |
| Change in MAP (mean, 95% CI) | +20.5 [19.5, 21.5] | +8.3 [7.1, 9.5] | +3.2 [2.8, 3.7] | −1.4 [−2.0, −0.8] | +0.5 [−0.2, 1.2] | +7.4 [5.8, 9.0] |
| p-value | $<10^{-16}$ | $<10^{-16}$ | $<10^{-16}$ | 1 | 0.07 | $<10^{-16}$ |

TABLE 5

Heart rate (HR, beats per minute) in individual animals during isoflurane general anesthesia. CI = confidence interval, RR = respiratory rate.

|  | Animal | | | | | |
|---|---|---|---|---|---|---|
|  | 1 | 2 | 3 | 4 | 5 | 6 |
| HR before methylphenidate (mean, [95% CI]) | 401.0 [400.4, 401.7] | 390.5 [389.8, 391.2] | 351.7 [351.2, 352.1] | 359.3 [357.9, 360.6] | 357.6 [357.1, 358.2] | 361.3 [360.4, 362.1] |
| HR after 5 mg/kg IV Methylphenidate (mean, [95% CI]) | 386.8 [385.8, 388.4] | 383.3 [382.3, 384.4] | 365.5 [365.2, 365.9] | 360.0 [358.7, 361.3] | +6.4 [5.3, 7.5] | 358.6 [357.8, 359.5] |
| Change in HR (mean, 95% CI) | −14.2 [−15.9, −12.5] | −7.2 [−8.4, −5.9] | +13.9 [13.3, 14.5] | +0.72 [−1.19, 2.64] | +0.5 [−0.2, 1.2] | −2.6 [−3.8, −1.4] |
| p-value | 1 | 1 | $<10^{-16}$ | 0.2236 | $<10^{-16}$ | 1 |

Example 5

In Examples 1-4, the inventors demonstrated that methylphenidate (MPH) actively induces emergence from isoflurane general anesthesia. Propofol is a widely used intravenous (IV) general anesthetic that may act by different receptor mechanisms than isoflurane. Thus, the inventors assessed if MPH induces emergence from other types of anesthesia, e.g., propofol anesthesia.

For the first experiment, a lateral tail vein IV catheter was placed in rats under isoflurane anesthesia. After full recovery, propofol (8 mg/kg) was administered IV and 45 sec later, MPH (5 mg/kg) or normal saline (NS, vehicle) was injected IV. Time to emergence was defined as the time until restoration of righting occurred. Statistical analysis was performed using the Mann-Whitney test.

In the first experiment, time to emergence after a single dose of propofol was 747±58 sec (mean±SE) for rats that received NS (n=6), and 433±24 sec (mean±SE) for rats that received MPH (n=6). The difference was statistically significant (p=0.002).

Figure 8:
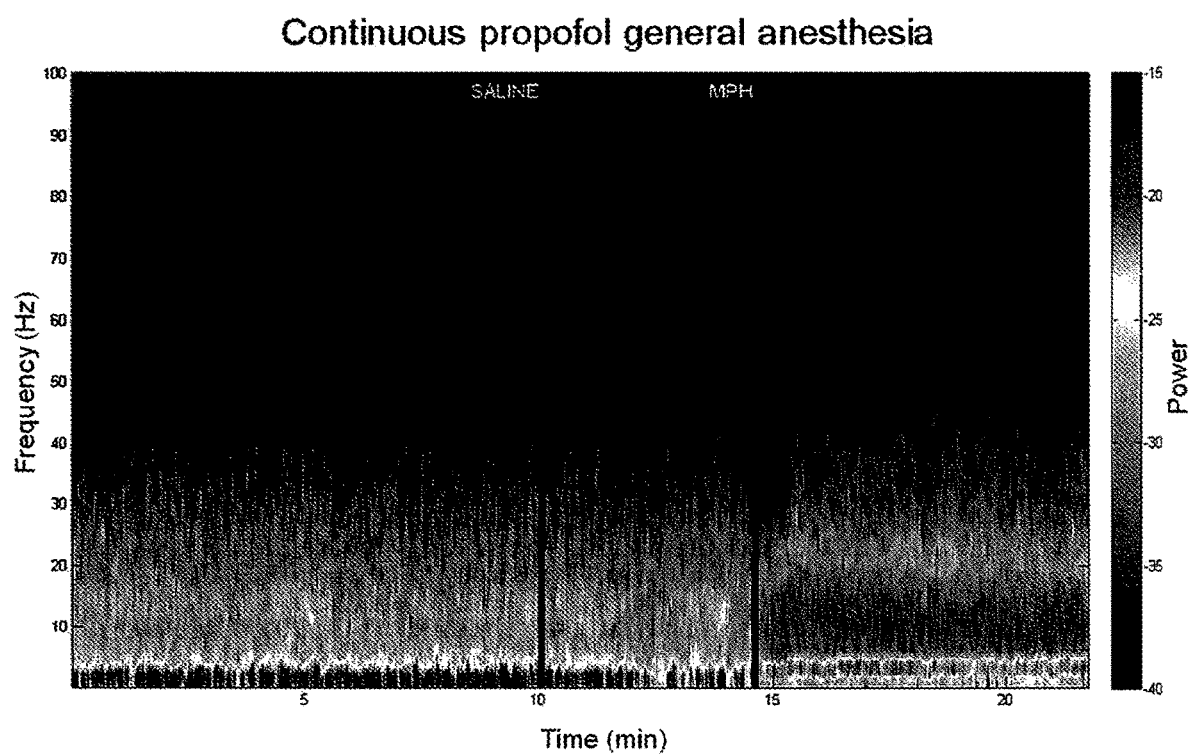
FIG. 8 shows EEG spectral analysis of the righting of a rat as demonstrated by a shift in power from delta (<4 Hz) to theta (4-8 Hz) after administration of MPH during continuous propofol anesthesia.

For the second experiment, 2 IV catheters were placed and a continuous propofol infusion was started in rats with pre-implanted EEG electrodes. After establishing the minimum plasma concentration of propofol required to maintain loss of righting, the second IV catheter was flushed with NS, and 5 minutes later MPH (5 mg/kg) was administered. In the second experiment with continuous propofol anesthesia, none of the rats exhibited purposeful movements after injection of NS. After MPH, however, 5/6 rats exhibited signs of arousal and had restoration of righting within 4 min. One rat had a delayed arousal response with restoration of righting 25 min after MPH. As shown in FIG. 8, EEG spectral analysis demonstrated a shift in power from delta (<4 Hz) to theta (4-8 Hz) after administration of MPH during continuous propofol anesthesia.

Accordingly, the inventors demonstrated that MPH decreases time to emergence after a single dose of propofol, and produces both behavioral and neurophysiological evidence of arousal during continuous propofol anesthesia. MPH may be clinically useful as a reversal agent for propofol.

Example 6

In this study, the inventors demonstrate that methylphenidate actively induces emergence from isoflurane anesthesia by increasing arousal. In addition, the inventors demonstrate using plethysmography and blood gas experiments that methylphenidate also increases minute ventilation, which increases the rate of anesthetic elimination from the brain.[20] Emergence from isoflurane anesthesia is dose dependent,[21] therefore methylphenidate-induced ventilatory stimulation likely contributes to accelerating time to emergence.

The inventors protocol for testing loss of righting reflex did not utilize a rotating anesthetizing chamber, and the average dose of isoflurane required to maintain loss of righting in this study was 0.9%. This dose was slightly higher than the dose previously reported for loss of righting in uninstrumented mice using a rotating anesthetizing chamber (0.81% isoflurane, with a 95% confidence interval between 0.78% and 0.84%).5 The stimulation provided by the temperature probe and the IV catheter in these rats was likely comparable to the stimulation provided by the rotating anesthetizing chamber in uninstrumented mice. Electroencephalogram and plethysmography studies were performed separately from behavioral experiments with some modifications in the experimental protocols designed to minimize motion artifacts. Electroencephalogram studies performed under very similar experimental conditions as the behavioral studies demonstrated a consistent shift from delta to theta power within 30 seconds of methylphenidate administration. These results agree with a previous study that reported methylphenidate induces a theta rhythm in rats anesthetized with chloral hydrate.[22] The plethysmography experiments performed at a higher dose of isoflurane (1.5%, or approximately 1 MAC) demonstrated increases in respiratory rate and minute ventilation. Thus, the inventors demonstrate herein that these changes are similar to the changes that would have been observed in animals that regained the righting reflex in the behavioral studies.

Cholinergic arousal pathways have been studied most extensively in the context of emergence from general anesthesia. Hudetz and colleagues[3] previously reported that intraventricular administration of the cholinesterase inhibitor neostigmine to rats during isoflurane anesthesia produced an increase in cross-approximate entropy of the electroencephalogram, and elicited behavioral signs of arousal such as spontaneous limb movements and orofacial explorative movements Alkire and colleagues' previously reported that injection of nicotine into the central medial thalamus induced return of righting during continuous inhalation of sevoflurane, providing evidence for cholinergic pathways that activate the thalamus inducing arousal from general anesthesia. In patients, physostigmine (PHY) has been reported to reduce post-operative somnolence after halothane general anesthesia.[23] In studies involving human volunteers, physostigmine (PHY) reversed propofol-induced loss of consciousness in 9 of 11 subjects,[24] and reversed sevoflurane-induced loss of consciousness in 5 of 8 subjects.[25] Both of these studies reported that administration of physostigmine produced significant increases in auditory steady-state response and bispectral index, which are neurophysiological correlates of increased arousal. Orexinergic arousal pathways have also been shown to play an important role in emergence from general anesthesia. Orexins are arousal-promoting peptide neurotransmitters released by neurons in the periformical area of the hypothalamus, and abnormal orexinergic signaling leads to narcolepsy.[26,27] Mesa and colleagues[28] have reported that a patient suffering from narcolepsy underwent 3 different operations between 1979 and 1995, and required 8-10 hours to emerge from general anesthesia each time. Kelz and colleagues[5] reported in mice that both genetic and pharmacologic ablation of orexinergic signaling delays time to righting after discontinuation of isoflurane or sevoflurane general anesthesia. Interestingly, the inhaled anesthetic concentration required to produce loss of righting was unchanged in orexin-ablated mice compared to wild-type, indicating that orexinergic neurons are not involved in the mechanisms underlying induction of general anesthesia. In a separate study by Zecharia et al.,[29] intraventricular administration of orexin-A was reported to reduce time to righting after propofol and dexmedetomidine administration.

Although there are several monoaminergic arousal pathways, they have been less well studied in the context of emergence from general anesthesia. Luo and Leung[6] have reported that injection of histamine into the basal forebrain of rats decreased time to righting after isoflurane general anesthesia, increased respiratory rate, and shifted electroencephalogram activity from a burst suppression pattern ("deep" general anesthesia) to a delta pattern ("lighter" general anesthesia). Their results suggest that enhanced histaminergic neurotransmission in the basal forebrain may also play a role in emergence from general anesthesia.

Decades ago, the clinical utility of methylphenidate as an analeptic, i.e. a central nervous system stimulant, was explored in psychiatry and anesthesiology 30 However, at that time, its mechanism of action was unknown. Psychiatrists reported using the drug to promote arousal in patients suffering from overdoses of antipsychotic nnedications,[31] and to facilitate psychiatric interviewing.[32] Studies conducted in the perioperative period suggested that methylphenidate promoted faster recovery after general anesthesia.[33,34] However, the only placebo-controlled, double-blinded study reported no difference in recovery time.[35] Prior to the United States Food and Drug Administration's black box warning on droperidol in 2001, the drug was widely used in anesthesiology practices as a sedative and antiemetic. The inventors demonstrate herein that the widespread use of droperidol may have confounded the results of some of the earlier clinical studies of methylphenidate (MPH). On the other hand, because methylphenidate (MPH) is now widely prescribed to treat attention deficit hyperactivity disorder (ADHD), there are recent reports of increased anesthetic requirements in patients who take nnethylphenidate.[36,37] These reports are consistent with the inventors discovery that methylphenidate (MPH) antagonizes isoflurane anesthesia. Methylphenidate (MPH) is known to inhibit dopamine and norepinephrine transporters with similar affinities ($Ki=250$ nM and 150 nM, respectively).[7] Dopaminergic neurons in the ventral tegmental area and substantia nigra pars compacta promote arousal, and play an important role in cognition and reward through projections to the thalamus, basal forebrain, nucleus accumbens, cortex, lateral dorsal tegmentum, and locus ceruleus.[38] A third cluster of wake-active, dopaminergic neurons has been recently identified in the ventral periaqueductal gray area.[39] There is recent evidence that enhancement of dopaminergic neurotransmission increases ventilatory drive in cats,[40-42].

Noradrenergic neurons in the locus ceruleus promote arousal through projections to the thalamus, basal forebrain, preoptic areas, and cortex,[2] and their inhibition is important in the sedative actions of propofol[43] and dexmedetomidine.[44] In addition, arousal-promoting histaminergic neurons arising from the tuberomammillary nucleus may also play a role in the actions of methylphenidate,[8] although the mechanisms underlying this pathway have yet to be clearly defined. Therefore methylphenidate likely induces emergence by enhancing arousal promoting monoaminergic (i.e. dopaminergic, noradrenergic, and possibly histaminergic) neurotransmission.

The inventors have demonstrated herein that administration of droperidol inhibits both the arousal-promoting effects and the increase in alveolar ventilation induced by methylphenidate during isoflurane general anesthesia. It has been reported that 3 mg/kg of droperidol has no effect on isoflurane potency in rats,[45] and that the EC50 for loss of righting in mice is 40 mg/kg,[46] suggesting that the relatively modest rodent dose of 0.5 mg/kg had little impact on the anesthetic state of the animals in this study. This conjecture is further supported by the lack of electroencephalogram changes observed in the animals after droperidol administration. Droperidol is known primarily as an antagonist at D2 dopamine receptors, but it has also been shown to inhibit al adrenergic receptors.[47,48] Therefore the inventors results with droperidol are consistent with the notion that dopaminergic and noradrenergic neurotransmission play important roles in methylphenidate induced emergence. Further studies will be necessary to elucidate which arousal pathways are responsible for the specific actions of methylphenidate, although it is likely that the simultaneous activation of multiple monoaminergic arousal pathways contributes to its efficacy.

Because the molecular mechanisms underlying the actions of general anesthetics are poorly understood, it has not been possible to design antagonists of general anesthetics. However, the inventors demonstrate that methylphenidate actively induces emergence from isoflurane anesthesia by stimulating monoaminergic arousal pathways. These results demonstrate a novel approach for identifying clinically useful antagonists of general anesthetics at the level of neural circuits. Methylphenidate has a well-established safety record in children and adults, through its more than two decades of use in the treatment of Attention Deficit Hyperactivity Disorder (ADHD).[7] The inventors demonstrate herein that intravenous methylphenidate could be used in adult and pediatric patients at the conclusion of surgery to reverse general anesthetic-induced unconsciousness and aid in the recovery of cognitive function.

REFERENCES

The reference cited herein are incorporated herein in their entirety by reference.

Brown E N, Lydic R, Schiff N D: General anesthesia, sleep, and coma. N Engl J Med 2010; 363: 2638-50

Franks N P: General anaesthesia: from molecular targets to neuronal pathways of sleep and arousal. Nat Rev Neurosci 2008; 9: 370-86

Hudetz A G, Wood J D, Kampine J P: Cholinergic reversal of isoflurane anesthesia in rats as measured by cross-approximate entropy of the electroencephalogram. Anesthesiology 2003; 99: 1125-31

Alkire M T, McReynolds J R, Hahn E L, Trivedi A N: Thalamic microinjection of nicotine reverses sevoflurane-induced loss of righting reflex in the rat. Anesthesiology 2007; 107: 264-72

Kelz M B, Sun Y, Chen J, Cheng Meng Q, Moore J T, Veasey S C, Dixon S, Thornton M, Funato H, Yanagisawa M: An essential role for orexins in emergence from general anesthesia. Proc Natl Acad Sci USA 2008; 105: 1309-14

Luo T, Leung L S: Basal forebrain histaminergic transmission modulates electroencephalographic activity and emergence from isoflurane anesthesia. Anesthesiology 2009; 111: 725-33

Heal D J, Cheetham S C, Smith S L: The neuropharmacology of ADHD drugs in vivo: insights on efficacy and safety. Neuropharmacology 2009; 57: 608-18

Horner W E, Johnson D E, Schmidt A W, Rollema H: Methylphenidate and atomoxetine increase histamine release in rat prefrontal cortex. Eur J Pharmacol 2007; 558: 96-7

Saper C B, Scammell T E, Lu J: Hypothalamic regulation of sleep and circadian rhythms. Nature 2005; 437: 1257-63

Van Dort C J, Baghdoyan H A, Lydic R: Adenosine A(1) and A(2A) receptors in mouse prefrontal cortex modulate acetylcholine release and behavioral arousal. J Neurosci 2009; 29: 871-81

Alkire M T, Asher C D, Franciscus A M, Hahn E L: Thalamic microinfusion of antibody to a voltage-gated potassium channel restores consciousness during anesthesia. Anesthesiology 2009; 110: 766-73

Vijn P C, Sneyd J R: I.v. anaesthesia and EEG burst suppression in rats: bolus injections and closed-loop infusions. Br J Anaesth 1998; 81: 415-21

Bokil H, Andrews P, Kulkarni J E, Mehta S, Mitra P P: Chronux: a platform for analyzing neural signals. J Neurosci Methods; 192: 146-51

Box G E P, Jenkins G M, Reinsel G C: Time series analysis: forecasting and control, 4th edition. Hoboken, N.J., John Wiley, 2008

Sheskin D J: Handbook of parametric and nonparametric statistical procedures, 2 edition. Boca Raton, Fla., Chapman Hall CRC, 2007, pp 577-587

Drorbaugh J E, Fenn W O: A barometric method for measuring ventilation in newborn infants. Pediatrics 1955; 16: 81-7

DeGroot M H, Schervish M J: Probability and statistics, 3rd edition. Boston, Addison-Wesley, 2002

Garkavi A L: Method of cyclic descent in the problem of best approximation. Mathematical Notes 1980; 27: 270-274

Pawitan Y: In all likelihood: Statistical modelling and inference using likelihood. Oxford, Oxford University Press, 2001

Eger E I: Anesthetic uptake and action. Baltimore, Williams & Wilkins, 1974

Friedman E B, Sun Y, Moore J T, Hung H T, Meng Q C, Perera P, Joiner W J, Thomas S A, Eckenhoff R G, Sehgal A, Kelz M B: A conserved behavioral state barrier impedes transitions between anesthetic-induced unconsciousness and wakefulness: evidence for neural inertia. PLoS One; 5: e11903

Hajos M, Siok C J, Hoffmann W E, Li S, Kocsis B: Modulation of hippocampal theta oscillation by histamine H3 receptors. J Pharmacol Exp Ther 2008; 324: 391-8

Hill G E, Stanley T H, Sentker C R: Physostigmine reversal of postoperative somnolence. Can Anaesth Soc J 1977; 24: 707-11

Meuret P, Backman S B, Bonhomme V, Plourde G, Fiset P: Physostigmine reverses propofol-induced unconsciousness and attenuation of the auditory steady state response and bispectral index in human volunteers. Anesthesiology 2000; 93: 708-17

Plourde G, Chartrand D, Fiset P, Font S, Backman S B: Antagonism of sevoflurane anaesthesia by physostigmine: effects on the auditory steady-state response and bispectral index. Br J Anaesth 2003; 91: 583-6

Chemelli R M, Willie J T, Sinton C M, Elmquist J K, Scammell T, Lee C, Richardson J A, Williams S C, Xiong Y, Kisanuki Y, Fitch T E, Nakazato M, Hammer R E, Saper C B, Yanagisawa M: Narcolepsy in orexin knockout mice: molecular genetics of sleep regulation. Cell 1999; 98: 437-51

Lin L, Faraco J, Li R, Kadotani H, Rogers W, Lin X, Qiu X, de Jong P J, Nishino S, Mignot E: The sleep disorder canine narcolepsy is caused by a mutation in the hypocretin (orexin) receptor 2 gene. Cell 1999; 98: 365-76

Mesa A, Diaz A P, Frosth M: Narcolepsy and anesthesia. Anesthesiology 2000; 92: 1194-6

Zecharia A Y, Nelson L E, Gent T C, Schumacher M, Jurd R, Rudolph U, Brickley S G, Maze M, Franks N P: The involvement of hypothalamic sleep pathways in general anesthesia: testing the hypothesis using the GABAA receptor beta3N265M knock-in mouse. J Neurosci 2009; 29: 2177-87 30. Adriani J, Drake P: Drug antagonists: their use in anesthesiology. Anesth Analg 1961; 40: 591-7

31. Ferguson J T, Linn F V, Nickels M M, Sheets J A, Jr.: Methylphenidate (ritalin) hydrochloride parenteral solution; preliminary report. J Am Med Assoc 1956; 162: 1303-4
32. Kerenyi A B, Koranyi E K, Sarwerfoner G J: The use of intravenous methylphenidate (ritalin) in psychiatric interviewing. Can Med Assoc J 1959; 80: 963-7
33. Gale A S: The effect of methylphenidate (ritalin) on thiopental recovery. Anesthesiology 1958; 19: 521-31
34. Dodson M E, Fryer J M: Postoperative effects of methylphenidate. Br J Anaesth 1980; 52: 1265-70
35. Roberts H: Postoperative administration of methylphenidate. Can Anaesth Soc J 1961; 8: 257-64
36. Kasuga T, Meno A, Honda M, Momoeda K, Nagase M, Hanaoka K: [General anesthesia for two patients taking methylphenidate (Ritalin)]. Masui 2008; 57: 748-51
37. Ririe D G, Ririe K L, Sethna N F, Fox L: Unexpected interaction of methylphenidate (Ritalin) with anaesthetic agents. Paediatr Anaesth 1997; 7: 69-72
38. Monti J M, Monti D: The involvement of dopamine in the modulation of sleep and waking. Sleep Med Rev 2007; 11: 113-33
39. Lu J, Jhou T C, Saper C B: Identification of wake-active dopaminergic neurons in the ventral periaqueductal gray matter. J Neurosci 2006; 26: 193-202
40. Lalley P M: Dopaminel receptor agonists reverse opioid respiratory network depression, increase $CO_2$ reactivity. Respir Physiol Neurobiol 2004; 139: 247-62
41. Lalley P M: D1-dopamine receptor agonists prevent and reverse opiate depression of breathing but not antinociception in the cat. Am J Physiol Regul Integr Comp Physiol 2005; 289: R45-51
42. Lalley P M: Opioidergic and dopaminergic modulation of respiration. Respir Physiol Neurobiol 2008; 164: 160-7
43. Nelson L E, Guo T Z, Lu J, Saper C B, Franks N P, Maze M: The sedative component of anesthesia is mediated by GABA(A) receptors in an endogenous sleep pathway. Nat Neurosci 2002; 5: 979-84
44. Nelson L E, Lu J, Guo T, Saper C B, Franks N P, Maze M: The alpha2-adrenoceptor agonist dexmedetomidine converges on an endogenous sleep-promoting pathway to exert its sedative effects. Anesthesiology 2003; 98: 428-36
45. Tanifuji Y, Zhang Y, Liao M, Eger E I, 2nd, Laster M J, Sonner J M: Do dopamine receptors mediate part of MAC? Anesth Analg 2006; 103: 1177-81
46. Germane S K: Droperidol—A Drug for Neurolepanesthesia and for Arresting Hypertonic Crises. Farmatsevticheskii Zhurnal 1978; 12: 146-149
47. McKeage K, Simpson D, Wagstaff A J: Intravenous droperidol: a review of its use in the management of postoperative nausea and vomiting. Drugs 2006; 66: 2123-47
48. Hyatt M, Muldoon S M, Rorie D K: Droperidol, a selective antagonist of postsynaptic alpha-adrenoceptors in the canine saphenous vein. Anesthesiology 1980; 53: 281-6

The invention claimed is:

1. A computerized method for determining a state of consciousness using electroencephalogram ("EEG") signals acquired from electrodes configured to be coupled to a subject experiencing an administration of at least one anesthetic agent or at least one drug to facilitate emergence from anesthesia, the computerized method comprising:
acquiring EEG data from the electrodes coupled to the subject;
applying at least one window to the EEG data;
for the at least one window, calculating a multi-taper spectrum estimation; and
based on the multi-taper spectrum estimation, generating an indicator about the state of consciousness of the subject, wherein the indicator includes a spectrogram.

2. The method of claim 1 further comprising determining physiological effects of the at least one anesthetic agent or at least one drug to facilitate emergence from anesthesia using the spectrogram and indicating the physiological effects in the indicator.

3. The method of claim 2 wherein determining physiological effects includes comparing the spectrogram to reference spectrograms.

4. The method of claim 1 further comprising determining a therapeutically effective amount of the at least one anesthetic agent or at least one drug to facilitate emergence from anesthesia using the indicator.

5. The method of claim 4 wherein determining a therapeutically effective amount includes comparing the indicator to reference reports.

6. The method of claim 1 wherein the sliding window has a duration of 2 seconds.

7. The method of claim 1 wherein applying at least one window includes applying a sliding window stepped through a 0.05 second interval.

8. The method of claim 1 wherein applying at least one window includes applying a sliding window.

9. The method of claim 1 wherein calculating the multi-taper spectrum estimation includes using 5 tapers.

10. The method of claim 1 wherein applying at least one window includes applying a sliding window.

11. The method of claim 10 wherein the sliding window includes a duration of 2 seconds.

* * * * *

UNITED STATES PATENT AND TRADEMARK OFFICE
CERTIFICATE OF CORRECTION

PATENT NO. : 11,553,876 B2
APPLICATION NO. : 16/373498
DATED : January 17, 2023
INVENTOR(S) : Emery N. Brown et al.

Page 1 of 1

It is certified that error appears in the above-identified patent and that said Letters Patent is hereby corrected as shown below:

In the Specification

Column 2, Line 7, "Aorexinergic,$^5$" should be --orexinergic,$^5$--.

Column 19, Line 65, "CARINA$^{TM}$" should be --CARIM$^{TM}$--.

Column 45, Lines 59-60, "paranneters.$^{14}$" should be --parameters.$^{14}$--.

Column 53, Line 47, "colleagues'" should be --colleagues$^4$--.

Column 54, Line 31, "nnedications,$^{31}$" should be --medications,$^{31}$--.

Column 54, Lines 34-35, "anesthesia.$^{3334}$" should be --anesthesia.$^{33,34}$--.

Column 54, Lines 46-47, "nnethylphenidate.$^{36,37}$" should be --methylphenidate.$^{36,37}$--.

Column 55, Line 19, "al" should be --α1--.

Column 57, Line 46, "Dopaminel" should be --Dopamine1--.

Signed and Sealed this
Fourth Day of April, 2023

Katherine Kelly Vidal
*Director of the United States Patent and Trademark Office*